US009579256B2

(12) United States Patent
Einy et al.

(10) Patent No.: US 9,579,256 B2
(45) Date of Patent: Feb. 28, 2017

(54) DEVICES, SYSTEMS AND METHODS FOR FILLING A SYRINGE WITH A MEDICATION

(71) Applicant: RESCU DOSE LTD., Haifa (IL)

(72) Inventors: Gilad Einy, Haifa (IL); Daniel Messinger, Migdal Haemek (IL)

(73) Assignee: RESCUE DOSE LTD, Haifa (IL)

( * ) Notice: Subject to any disclaimer, the term of this patent is extended or adjusted under 35 U.S.C. 154(b) by 0 days.

(21) Appl. No.: 14/906,149

(22) PCT Filed: Jul. 17, 2014

(86) PCT No.: PCT/IL2014/050654
§ 371 (c)(1),
(2) Date: Jan. 19, 2016

(87) PCT Pub. No.: WO2015/008292
PCT Pub. Date: Jan. 22, 2015

(65) Prior Publication Data

US 2016/0158105 A1 Jun. 9, 2016

Related U.S. Application Data

(60) Provisional application No. 61/847,148, filed on Jul. 17, 2013.

(51) Int. Cl.

| | |
|---|---|
| ***A61B 19/00*** | (2006.01) |
| ***A61J 1/20*** | (2006.01) |
| ***B65B 3/00*** | (2006.01) |
| ***A61J 1/16*** | (2006.01) |
| ***B65B 3/04*** | (2006.01) |

(52) U.S. Cl.
CPC . *A61J 1/20* (2013.01); *A61J 1/16* (2013.01); *A61J 1/2096* (2013.01); *B65B 3/003* (2013.01); *B65B 3/04* (2013.01)

(58) Field of Classification Search
CPC ... A61J 1/16; A61J 1/20; A61J 1/2096; B65B 3/003; B65B 3/04
USPC .................................................. 604/403–416
See application file for complete search history.

(56) References Cited

U.S. PATENT DOCUMENTS

2009/0108018 A1* 4/2009 Li ........................ A61J 1/2096 221/156
2012/0241042 A1 9/2012 Strangis

* cited by examiner

*Primary Examiner* — Philip R Wiest
(74) *Attorney, Agent, or Firm* — Mark David Torche; Patwrite Law

(57) ABSTRACT

Devices, systems and methods for automatically positioning a syringe in a target orientation suitable for withdrawing medication from a container, and for filling the syringe with the medication. The device comprises a syringe conveyor, which is configured to receive the syringe in an initial orientation, and to bring the syringe to a target orientation by being translated and rotated while holding the syringe in a steady orientation relative to the syringe conveyor. The device further comprises a supporting module, configured to support the syringe conveyor while allowing a translation and a rotation thereof. The device comprises a syringe holder configured to hold the syringe, and a gripper coupled to the syringe holder. The gripper is configured to engage the plunger and to enable the automatic displacement.

14 Claims, 20 Drawing Sheets

DEVICES, SYSTEMS AND METHODS FOR FILLING A SYRINGE WITH A MEDICATION

CROSS-REFERENCE TO RELATED APPLICATIONS

This patent application is a U.S. National Phase filing of co-pending, commonly owned PCT Patent Application No. PCT/IL2014/050654, filed on Jul. 17, 2014, which is based upon and claims the benefit of the filing date of commonly owned U.S. Provisional Patent Application Ser. No. 61/847, 148, filed on Jul. 17, 2013, each of which is incorporated herein by reference in its entirety.

FIELD OF THE INVENTION

The invention relates to filling syringes. More specifically the invention relates to automatically filling syringes with medications.

BACKGROUND OF THE INVENTION

Automatically filling syringes has many known advantages in the art. For example, US patent application 2009/0198208 to Straysky and Einy discloses a dosage dispenser intended to provide a solution for measuring and dilution of liquid medications and issuing marked and ready for use. The dosage dispenser device carries out actions required for the preparation of a required dose of medication, including identifying ampoules, breaking them, filling a syringe, diluting the medication in a solution, marking the syringe, disposing of waste and documenting the process, all at the patient bedside. The dosage dispenser is aimed at reducing the number of errors in the dosage, which is a problem, menacing medical services throughout the world. The problem is made acute by considerable pressure on the medical teams while carrying out many and complex procedures under pressure in a situation of uncertainty and with variable data.

SUMMARY OF THE INVENTION

The invention discloses devices and systems for automatically filling syringes, and methods for utilization thereof.

In an embodiment, a device for automatically positioning a syringe in an orientation suitable for withdrawing medication from a container, the device comprising: a syringe conveyor configured to receive the syringe in an initial orientation, and to bring the syringe to a target orientation by being translated and rotated while holding the syringe in a steady orientation relative to the syringe conveyor, wherein the target orientation, which is suitable for withdrawing medication from the container, is one of an upward orientation and a downward orientation, and the initial orientation is different from the target orientation, and wherein in the upward orientation a tip of the syringe is pointing downward and in the downward orientations the tip is pointing upward; and a supporting module configured to support the syringe conveyor while allowing a translation and a rotation thereof; wherein the supporting module and the syringe conveyor are jointly configured to mechanically derive the rotation from the translation.

In an embodiment, the syringe conveyor comprises: a syringe carrier configured to be translated and rotated; wherein the syringe carrier and the supporting module are jointly configured to mechanically derive the rotation from the translation; and a syringe holder configured to hold the syringe in a steady orientation relative to the syringe carrier.

In an embodiment, the device further comprises: a linear actuator coupled to the supporting module and to the syringe conveyor, configured to translate the syringe conveyor relative to the supporting module.

In an embodiment, the supporting module comprises a first member, and the syringe conveyor comprises a second member, the first and second members are jointly configured to engage each other during the translation, thereby inducing the rotation.

In an embodiment, the first member is a rack and the second member is a pinion.

In an embodiment, one of the first and second members is a protrusion and another one of the first and second members is a socket configured to engage the protrusion.

In an embodiment, one of the first and second members is a plurality of protrusions, and another one of the first and second members is a plurality of sockets configured to engage the protrusions.

In an embodiment, a device for holding a barrel of a syringe and a plunger of the syringe in order to allow automatic translation of the plunger inside the barrel, the device comprising: a syringe holder configured to hold the syringe; a lock mechanism configured to stabilize the barrel of the syringe relative to the syringe holder; a gripper coupled to the syringe holder and jointly configured therewith to enable the gripper to engage the plunger by changing a relative angle between the gripper and the syringe holder; wherein the gripper, the syringe holder and the lock mechanism are jointly configured to enable the automatic displacement.

In an embodiment, the device further comprises: a gripper holder configured to hold the gripper; wherein the gripper holder and the syringe holder are jointly configured to be translated in parallel, and to be rotated relative to each other, thereby changing the relative angle; and a syringe carrier configured to support the syringe holder and the gripper holder, to allow a translation of the syringe holder and the gripper holder with respect to the syringe carrier, and to allow a relative rotation of the syringe holder and the gripper holder with respect to each other; wherein the syringe carrier, the syringe holder, and the gripper holder, are jointly configured to mechanically derive the relative rotation from the translation.

In an embodiment, the device further comprises a linear actuator coupled to the syringe carrier, the syringe holder, and the gripper holder, and configured to drive the translation.

In an embodiment, the syringe carrier comprises a first member; at least one of the syringe holder and the gripper holder comprises a second member; the first and second members are jointly configured to be engaged during the translation, thereby causing a rotation of the at least one of the syringe holder and the gripper holder.

In an embodiment, the first member is a rack, and the second member is a pinion.

In an embodiment, the first member is a protrusion, and the second member is a socket.

In an embodiment, the second member is a protrusion, and the first member is a socket.

In an embodiment, a system for automatically drawing medication into a syringe, the system comprising: a first device configured to receive the syringe in an initial orientation, and to automatically position the syringe in a target orientation suitable for drawing medication from the container by utilizing a first translation and by further utilizing a first rotation mechanically derived from the first translation, wherein the target orientation is one of an upward orientation and a downward orientation, and the initial orientation is different from the target orientation; in the upward orientation a tip of the syringe is pointing downward and in the downward orientations the tip of the syringe is pointing upward; a second device configured to allow an automatic displacement of a plunger of the syringe inside a barrel of the syringe by holding the barrel, holding the plunger, and translating the plunger relative to the barrel; and a third device configured to enable a needle coupled to the syringe, whereupon the syringe is held in the target orientation, to reach the medication in the container by reducing a distance between the container and the syringe.

In an embodiment, the first device comprises: a syringe conveyor configured to receive the syringe in the initial orientation, and to bring the syringe to the target orientation by being translated and rotated while holding the syringe in a steady orientation relative to the syringe conveyor; and a supporting module configured to support the syringe conveyor while allowing a translation and a rotation thereof; wherein the first supporting module and the syringe conveyor are jointly configured to mechanically derive the rotation from the translation.

In an embodiment, the syringe conveyor comprises: a syringe carrier configured to be translated and rotated; wherein the syringe carrier and the supporting module are jointly configured to mechanically derive the rotation from the translation; and a syringe holder configured to hold the syringe in a steady position relative to the syringe carrier.

In an embodiment, the first device comprises: a syringe carrier configured to be translated and rotated; and a syringe holder configured to hold the syringe in a fixed position relative to the syringe carrier.

In an embodiment, the second device comprises: a lock mechanism configured to stabilize the barrel of the syringe relative to the syringe holder; and a gripper coupled to the syringe holder and jointly configured therewith to enable the gripper to engage the plunger by changing a relative angle between the gripper and the syringe holder; wherein the gripper, the syringe holder, and the lock mechanism are jointly configured to enable the automatic displacement.

In an embodiment, the second device further comprises: a gripper holder configured to hold the gripper; wherein the gripper holder and the syringe holder are jointly configured to be translated in parallel, and to be rotated relative to each other, thereby changing the relative angle; and a syringe carrier configured to support the syringe holder and the gripper holder, to allow a translation of the syringe holder and the gripper holder with respect to the syringe carrier, and to allow a relative rotation of the syringe holder and the gripper holder with respect to each other; wherein the syringe carrier, the syringe holder, and the gripper holder, are jointly configured to mechanically derive the relative rotation from the translation.

In an embodiment, a system for automatically drawing medication into a syringe, the system comprising: a first device configured to receive the syringe in an initial orientation, and to automatically position the syringe in a target orientation suitable for drawing medication from the container, wherein the target orientation is one of an upward orientation and a downward orientation, and the initial orientation is different from the target orientation, and wherein in the upward orientation a tip of the syringe is pointing downward and in the downward orientations the tip is pointing upward; a second device configured to allow an automatic displacement of a plunger of the syringe inside a barrel thereof by holding the barrel, holding the plunger, and translating the plunger relative- to the barrel; and a third device configured to enable a needle coupled to the syringe to reach the medication by reducing a distance between the container and the syringe, while the syringe is held in the target orientation; wherein horizontal dimensions of the system allow placing the system within a rectangular cuboid whose maximal width is 15 centimeters.

In an embodiment, the horizontal dimensions of the system allow placing the system within a rectangular cuboid whose maximal width is 10 centimeters.

In an embodiment, the horizontal dimensions of the system allow placing the system within a rectangular cuboid whose maximal length is 50 centimeters.

In an embodiment, the horizontal dimensions of the system allow placing the system within a rectangular cuboid whose maximal floor area is 1000 square centimeters.

In an embodiment, a method for automatically drawing medication into a syringe, the method comprising: receiving the syringe in an a first orientation; utilizing a translation and a rotation for automatically positioning the syringe in a second orientation suitable for drawing medication from the container, wherein in one of the first and second orientations a tip of the syringe is pointing downward and in other one of the first and second orientations a tip of the syringe is pointing upward; and wherein the first rotation is mechanically derived from the first translation; automatically reducing a distance between the container and the syringe, while the syringe is held in the second orientation, thereby enabling a needle coupled to the syringe to reach the medication; automatically holding a barrel of the syringe; and automatically translating the plunger inside the barrel, thereby drawing medication into a syringe.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION

Figure 2A:
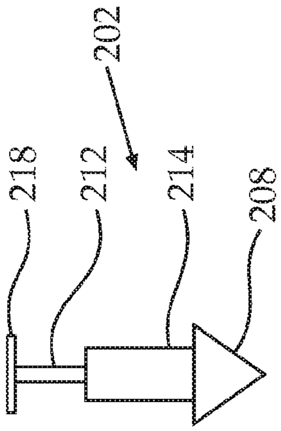
FIGS. 2A-2E symbolically illustrate snapshots of a syringe subject to automatic filling with a medication that is withdrawn from a container, while in a downward orientation, in accordance with some embodiments of the invention.

Before explaining some embodiments of the present invention, it should be appreciated that although various embodiments of the present invention are described herein, these embodiments are only given for the purpose of explaining the present invention, and the present invention should not be considered as being limited to and/or by these embodiments, while it should be appreciated that it would be possible to implement the present invention in various other ways.

In the following description, components that are common to more than one figure will be referenced by the same reference numerals.

In addition, unless specifically noted, embodiments described or referenced in the present description can be additional and/or alternative to any other embodiment described or referenced therein.

Figure 1:
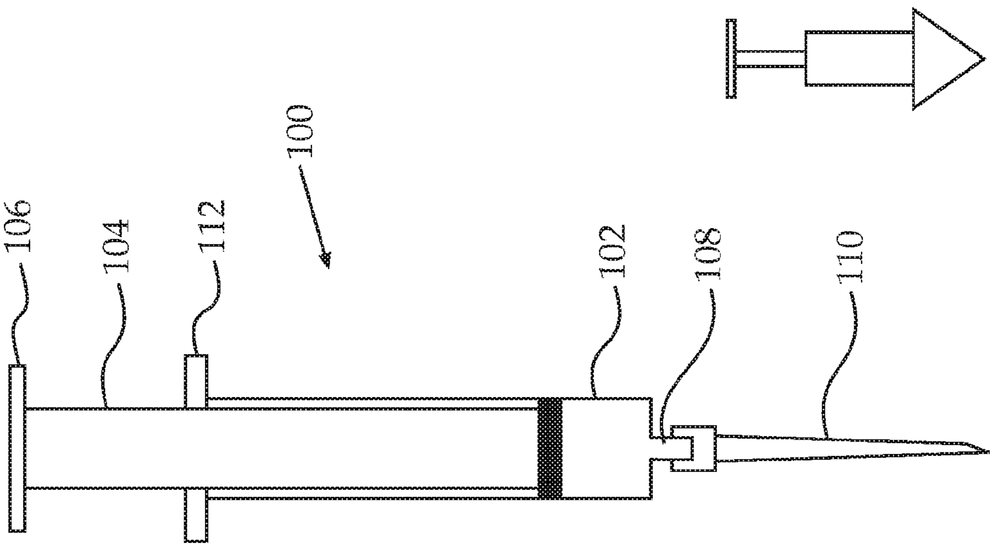
FIG. 1 illustrates a known in the art syringe.

FIG. 1 illustrates a syringe 100, as is known in the art. A syringe generally comprises a barrel 102 configured to contain medication, and a plunger 104 configured to be translated within the barrel, thereby drawing medication into the barrel and/or withdrawing medication from the barrel. The plunger 104 may comprise a top 106, which may be utilized for translating the barrel by pulling and/or pushing the top. A syringe may further comprise a tip 108 configured for attaching a needle 110 thereto. The needle may be a hypodermic needle, or any other elongated hollow article configured to be attached to the tip of the syringe, and to enable drawing medication therethrough into the barrel, e.g., from a container, and/or to enable injecting medication from the barrel, e.g., into a body or a container, etc. A syringe may also comprise a flange 112 coupled to the barrel, in order to enable holding the barrel firmly while translating the plunger relative to the barrel. It is noted though that syringe 100 has been brought as a general example only, while the invention is by no way limited to likewise syringes. Syringes applicable to the case may include other forms of syringes, other sizes and proportions of syringes, various materials from which a syringe is made of, etc.

Syringes are often used in medicine to administer injections, insert intravenous drugs into the bloodstream, etc. It should be appreciated that in some cases, it may be preferable to automatically draw medications into a syringe, instead of manually doing the same. For example, sometimes it is preferable to avoid contact with a medication due to hazards concerned with the medication. One non-limiting case in which preference of automatic drawing of a hazardous medication is demonstrated is preparation of a so-called "dose complex": a radioactive material to be injected into a body of a patient, e.g., during nuclear medicine diagnosis such as nuclear mapping. The dose complex is typically prepared in a central radiotherapy pharmacy or in various nuclear medicine centers (herein the term "radiotherapy pharmacy" is used to describe a central radiotherapy pharmacy, a nuclear medicine center, or any other laboratory that may prepare and manipulate dose complexes). Throughout the preparation of a dose complex, and during transport thereof to the clinical center where the dose complex should be injected to a patient, appropriate shielding is demanded, such as to avoid directly radiating individuals. Hence, further to preparing the dose complex it is typically drawn into syringes that are then placed in radiation protecting containers, such as a so-called shielded "pig", which is made of tungsten to shield radiation. The radiation protecting containers are typically used for transport of the prepared syringe to the clinical center, where the syringe is taken out of the container and the complex is injected to a patient directly from the syringe. However, today, the dispensing of the dose complex into syringes is manually administered, in hoods protecting the preparing technician from radiation. It should be appreciated, therefore, that automatically drawing radioactive medications into syringes and injecting radioactive medications from syringes, e.g., in such a radiotherapy pharmacy, is advantageous over manual handling.

However, the invention is not limited to radiotherapy pharmacies. Embodiments thereof may be applied also in case of other hazards concerned with medications, e.g., when a medication comprises a poisonous substance. Moreover, it may be desired to use embodiments of the invention due to other consideration additional or alternative to hazards. For example, in a clinic where the medical staff administers medications, amongst many should be injected, it should be appreciated that an automatic filling of syringes may be more accurate and therefore safe, and hence embodiments of the invention may be utilized therefor.

Some aspects of the present invention relate to devices and systems, for automatically drawing medications into syringes while the medications are withdrawn from containers, and for injecting medications from syringes, into containers or as waste. Some aspects relate also to methods for utilizing such devices and systems. The medication, which may be any substance utilized for treating human beings and/or animals, or possibly any other substance suitable for being drawn into a syringe, is contained in a container, for example a vial, an ampule, or any other suitable container. Some containers, such as open ampules, are configured for withdrawing the medication therefrom while the syringe is positioned in an "upward" position, when the top of the plunger is pointing upward, and the tip of the syringe is pointing downward. In the upward position, if there is a needle attached to the syringe, the needle is pointing downward, and the distal end of the needle can be inserted into the container (e.g. the ampule) through an opening thereof, thereby reaching the medication residing within the container. Other containers, for example vials, are configured for drawing the medication therefrom while the syringe is positioned in an "downward" position, when the top of the plunger is pointing downward, and the tip of the syringe is pointing upward. In the downward position, the needle is pointing upward, and its distal end can be inserted into the container (e.g. the vial) through a penetrable member thereof (e.g., a septum), thereby reaching the medication residing within the container. It is appreciated that "upward" and "downward" may be interpreted broadly as being inclined above or below the horizontal, respectively. Moreover, it is noted that the terms "upward" and "downward" as defined herein with reference to a syringe are non-limiting. In other cases alternative, opposite terms may be used, whereupon "upward" means that the plunger's top points down while the tip points up, and "downward" means that the top points up while the tip points down.

FIGS. 2A-2E symbolically illustrate snapshots of a syringe subject to automatic filling with a medication that is withdrawn from a container, while in a downward orientation, in accordance with some embodiments of the invention. FIG. 2A introduces a symbolic syringe, which is symbolically represented as an arrow 202. Accordingly, instead of referring to "arrow 202", hereinafter the arrow may be referred to as a "syringe 202". The arrow's sharp tip represents the distal end of a needle 208, and accordingly, instead of referring to "tip 208", hereinafter the tip may be referred to as a "needle 208". Similarly, the rectangle represents a barrel 214 and the T shaped rod represents a plunger 212 with a top 218. Syringe 202 may be an example of the syringe 100 in FIG. 1, or any other suitable syringe.

Figure 2B:
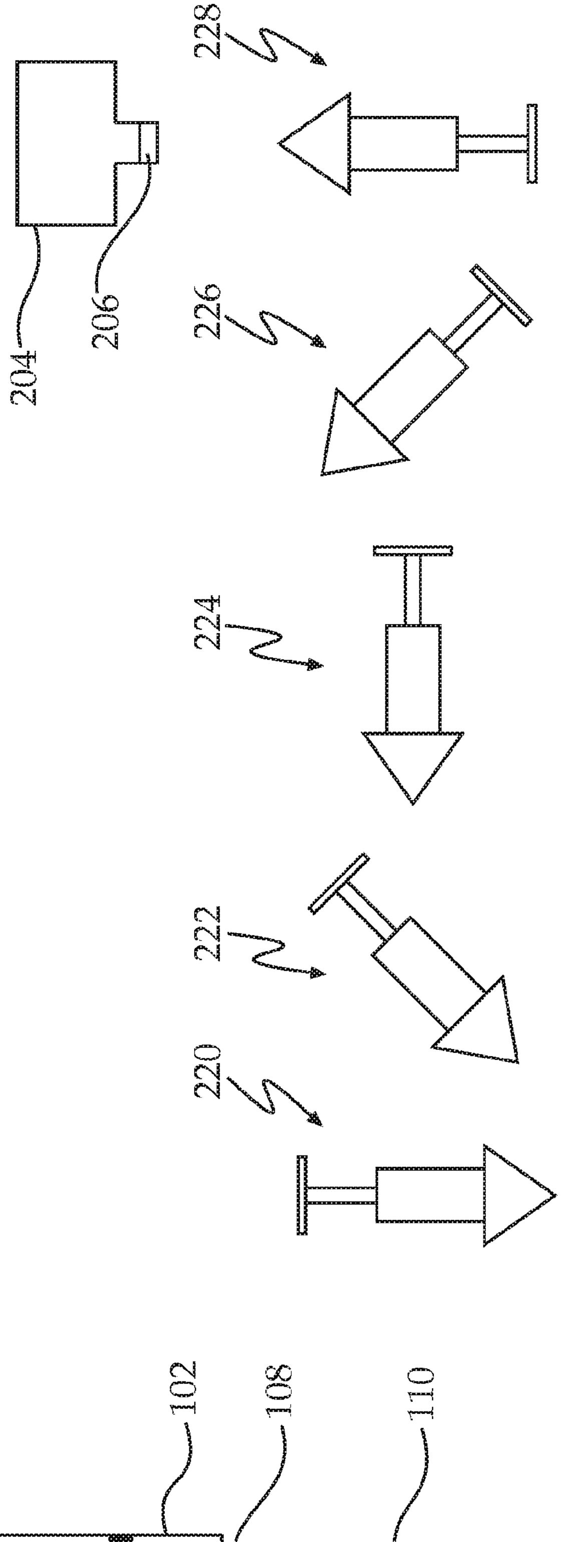

FIG. 2B symbolically illustrates snapshots of the syringe starting from an initial orientation 220, in which syringe 202 is received. In the illustrated example the initial orientation 220 of syringe 202 is an upward orientation. However, the initial orientation may be any orientation different from a downward orientation suitable for withdrawing medication from the vial, and it is by no way limited to the orientation illustrated in the figure. Then, the syringe is being translated and rotated, as represented by 222, 224 and 226, until it reaches its target orientation 228, whereupon it is positioned in a downward orientation beneath a container 204. Container 204 may be a vial comprising a septum 206, or any other container suitable for the case.

Figure 2E:
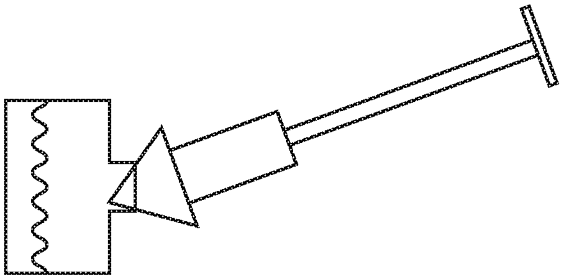
Figure 2D:
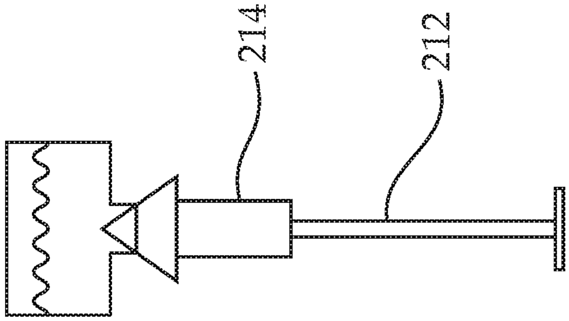
Figure 2C:
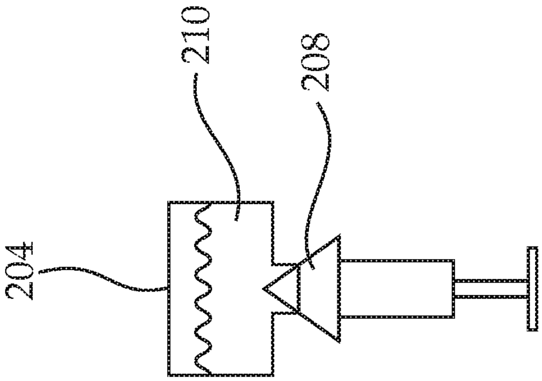

In FIG. 2C the syringe 228, residing beneath container 204, is advanced toward the container, thereby reducing the distance between the syringe and the container, until a distal end of needle 208 penetrates the container, and reaches a medication 210 residing therein. Additionally or alternatively to advancing the syringe toward the container, it should be appreciated that the distance between them can be reduced by advancing the container toward the syringe.

After the needle reaches the medication, plunger 212 of the syringe is being pulled out of the syringe barrel 214, thereby withdrawing medication from the container into the barrel, as illustrated in FIG. 2D. It is noted that although the downward orientation of the syringe is illustrated in FIGS. 2B to 2D as being strictly vertical, an inclined downward orientation, as illustrated in FIG. 2E, may be applicable for the case as well.

FIGS. 3A-3E symbolically illustrate snapshots of a syringe, subject to automatic filling with a medication that is withdrawn from a container while in an upward orientation, in accordance with some embodiments of the invention. A syringe 302 symbolically represented by an arrow, as has been done with reference to syringe 202 of FIGS. 2A-2E.

Figure 3A:
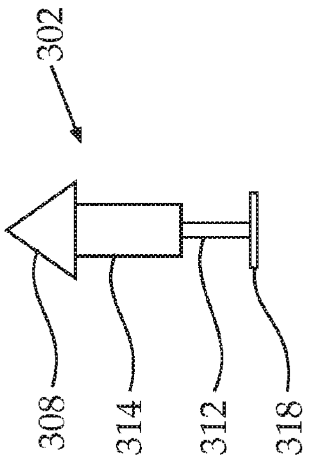
FIGS. 3A-3E symbolically illustrate snapshots of a syringe subject to automatic filling with a medication that is withdrawn from a container, while in a upward orientation, in accordance with some embodiments of the invention.

FIG. 3A introduces arrow 302 which represents syringe 302, which comprises a barrel 314, a plunger 312, a top 318 of plunger 312, and a needle 308. Syringe 302 may be an example of the syringe 100 in FIG. 1, or any other suitable syringe.

Figure 3B:
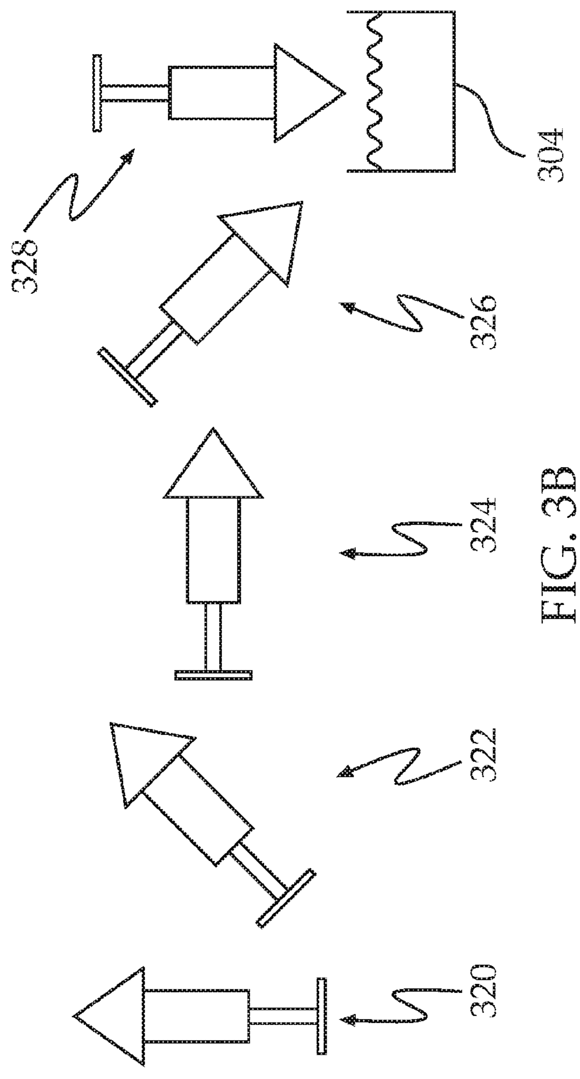

FIG. 3B symbolically illustrates snapshots of the syringe starting from an initial orientation 320, in which syringe 302 is received. In the illustrated example the initial orientation 320 of syringe 302 is a downward orientation. However, the initial orientation may be any orientation different from an upward orientation suitable for withdrawing medication from the vial in this example, and it is by no way limited to the orientation illustrated in the figure. Then, the syringe is being translated and rotated, as represented by 322, 324 and 326, until it reaches its target orientation 328, whereupon it is positioned in an upward orientation above a container 304. Container 304 may be an open ampule, or any other container suitable for withdrawal of medication from the container by a syringe in an upward orientation.

Figure 3C:
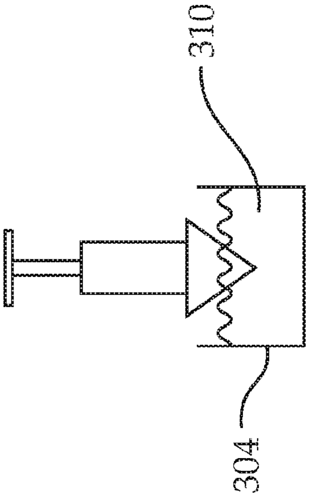

IN FIG. 3C syringe 302, residing above container 204 as illustrated in 328 of FIG. 3B, is advanced toward the container, thereby reducing the distance between the syringe and the container, until a distal end of needle 308 enters the container, and reaches a medication 310 residing therein. Additionally or alternatively to advancing the syringe toward the container, it should be appreciated that the distance between them can be reduced by advancing the container toward the syringe.

Figure 3D:
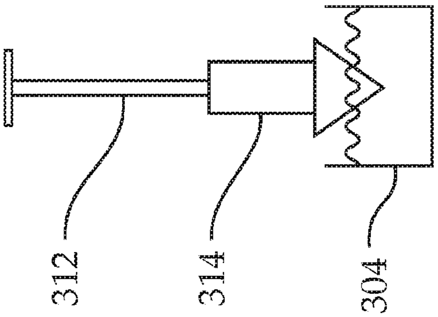
Figure 3E:
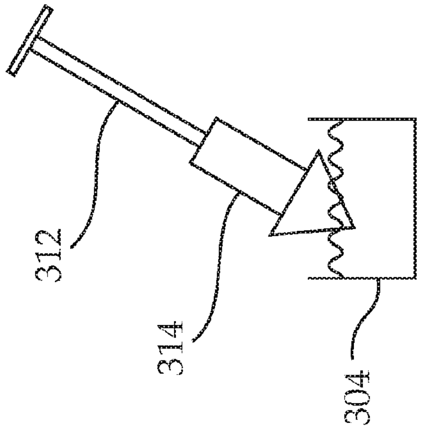

After the needle reaches the medication, plunger 312 of the syringe is being pulled out of the syringe barrel 314, thereby withdrawing medication from the container into the barrel, as illustrated in FIG. 3D. It is noted that although the upward orientation of the syringe is illustrated in FIGS. 2B to 2D as being strictly vertical, an inclined upward orientation, as illustrated in FIG. 3E, may be applicable for the case as well.

It should be appreciated that syringes 202 and 302 of FIGS. 2A-2E and 3A-3E are translated from their initial positions (220 and 320) to their target positions (228 and 328) beneath or above the containers, respectively. Furthermore, syringes 202 and 302 are rotated as well, syringe 202 from an upward orientation to a downward orientation and syringe 302 from a downward orientation to an upward orientation.

Further to introducing the translation and rotation operations involved in an automatic filling of syringes with reference to FIGS. 2A-2E and 3A-3E, embodiments of devices that perform such operations are disclosed below.

FIGS. 4A-4E, and FIGS. 7A-7E, schematically illustrate devices for automatically positioning a syringe relative to a container of a medication in an orientation suitable for withdrawing the medication from the container, according to certain embodiments of the invention. FIGS. 4A-4E, wherein the syringe is positioned in a downward orientation, are discussed in the following paragraphs, and FIGS. 7A-7E, wherein the syringe is positioned in a downward orientation, are discussed further below.

FIGS. 4A-4E schematically illustrate a device 400 for automatically positioning a syringe 402 in a downward orientation suitable for drawing medication from a container 400, according to certain embodiments of the invention. The syringe 402 may be, for example, a syringe similar to syringe 100 in FIG. 1 or any other syringe suitable for the case. Container 404 may be, e.g., a container similar to container 204 in FIG. 2, or any other container suitable for the case, such as a vial etc.

Device 400 further comprises a syringe conveyor 406, which is configured to receive the syringe in the initial orientation and to hold the syringe in a steady orientation relative to the syringe conveyor, i.e., wherein the orientation of syringe changes together with the orientation of the syringe conveyor.

Figure 4A:
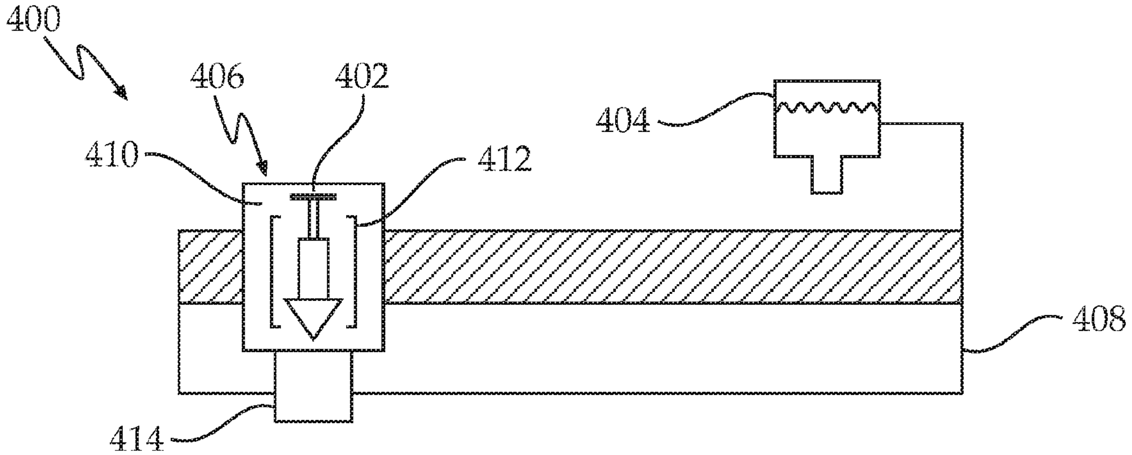
FIGS. 4A-4E schematically illustrate a device for automatically positioning a syringe in a downward orientation suitable for drawing medication from a container, according to some embodiments of the invention.
Figure 4B:
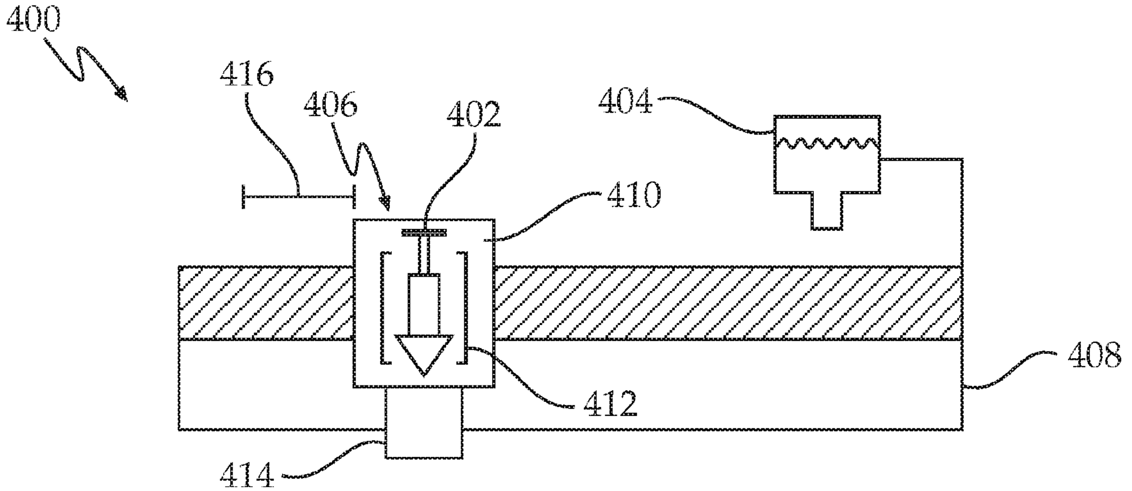
Figure 4C:
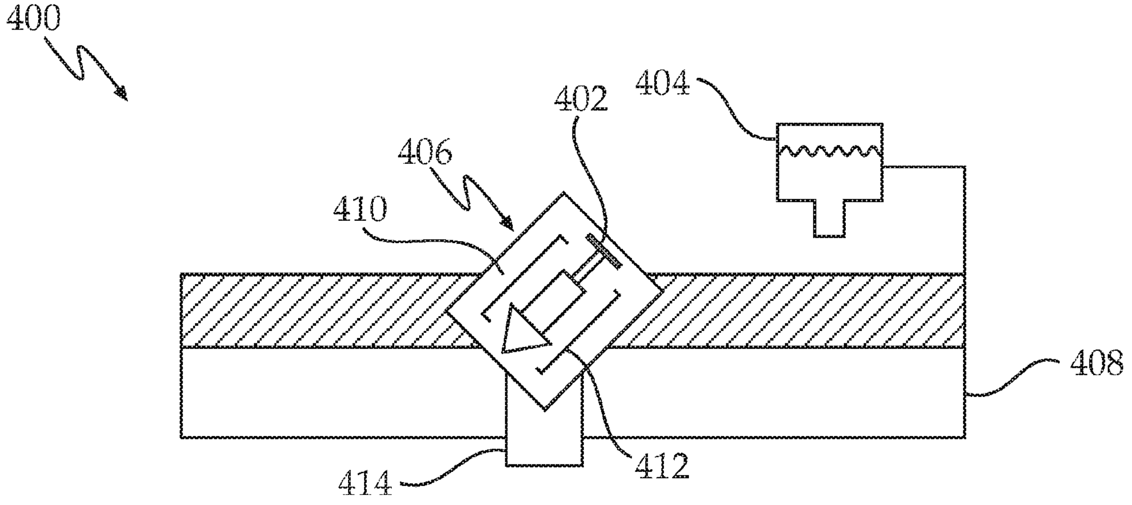
Figure 4D:
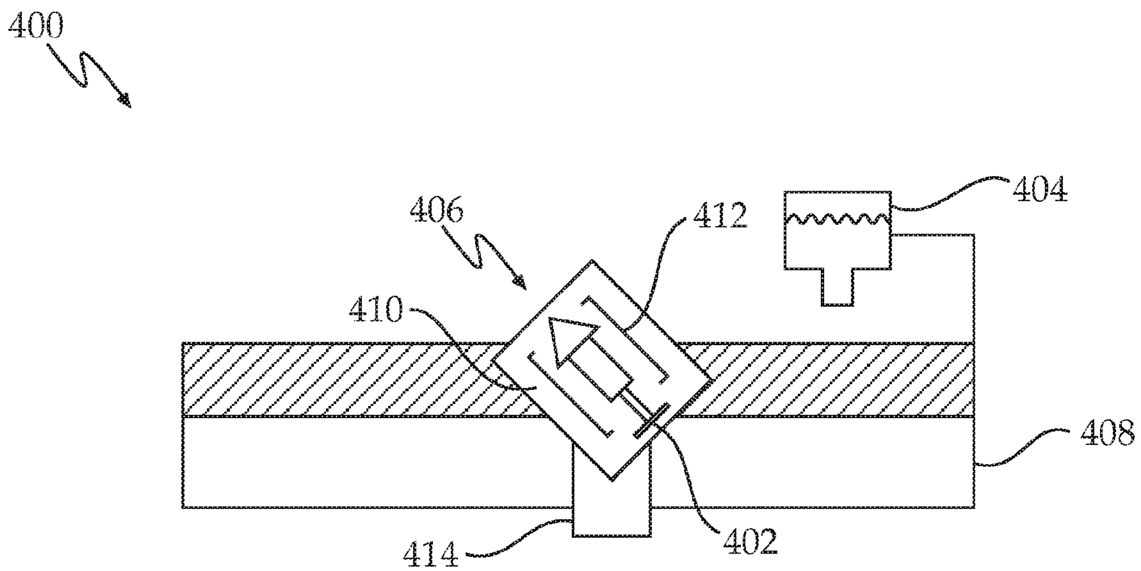

The syringe conveyor is further configured to be translated and rotated while holding the syringe, thereby bringing the syringe to a downward orientation beneath the container. The translation and rotation of the syringe conveyor are schematically illustrated in FIGS. 4A-4E, wherein FIG. 4A schematically illustrates the initial orientation, FIG. 4B depicts the syringe conveyor further to a translation thereof, wherein the translated distance is marked by 416, FIGS. 4C and 4D depict two snapshots along the rotation of the syringe conveyor and FIG. 4E schematically illustrates the syringe conveyor with a syringe in a downward orientation beneath the container.

Device 400 further comprises a supporting module 408, which is configured to support the syringe conveyor 406, while allowing the syringe conveyor to be translated and rotated. Furthermore, the supporting module is jointly configured with the syringe conveyor so that the rotation of the syringe conveyor is mechanically derived from the translation of the syringe conveyor. Therefore, in some embodiments, both the translation and the rotation of the syringe conveyor may be accomplished with a single actuator.

In some embodiments, syringe conveyor 406 may comprise a syringe carrier 410 and a syringe holder 412. The syringe carrier is configured to support the syringe holder, and the syringe holder is configured to hold the syringe in a steady position relative to the syringe carrier, It will be later described, with reference to FIGS. 8A-8D, that holding the syringe in the steady orientation allows a gripper to hold the plunger of the syringe. The syringe carrier is configured to be supported by the supporting module, and is configured to be translated and to be rotated relative to the supporting module, thereby translating and rotating the syringe. Furthermore, the syringe carrier is jointly configured with the supporting module to derive the rotation of the syringe carrier from the translation thereof.

Figure 4E:
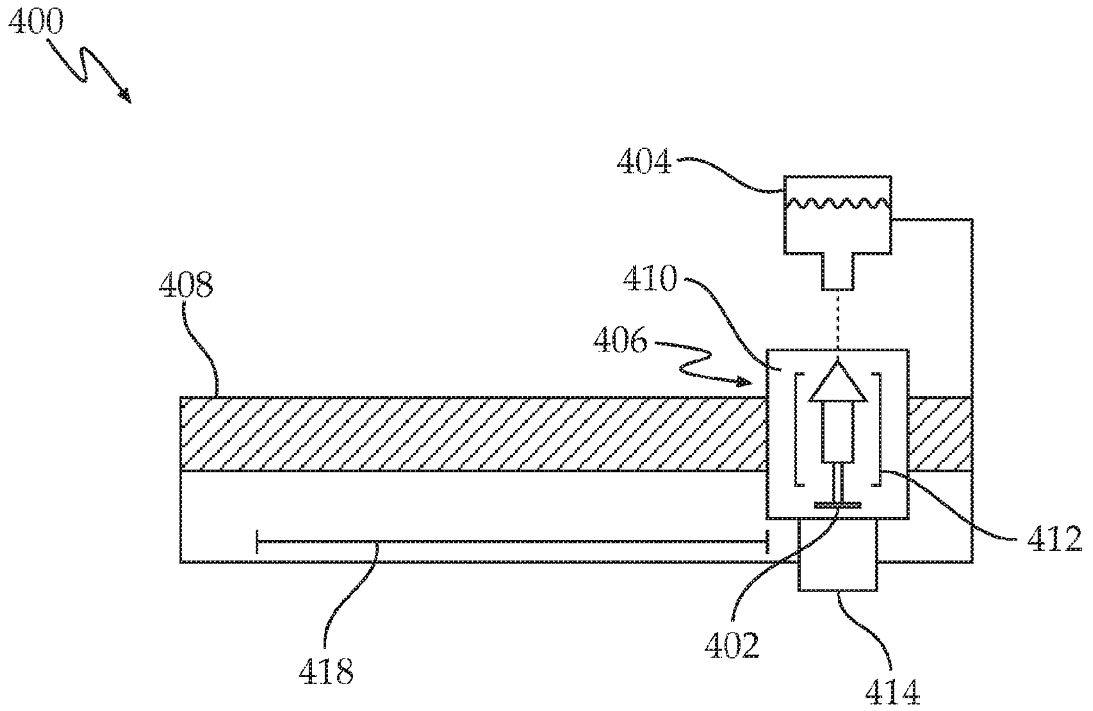

In some embodiments, device 400 may comprise a linear actuator 414 coupled to the supporting module and to the syringe conveyor, and configured to translate the syringe conveyor relative to the supporting module, thereby resulting in the translation of the syringe conveyor, e.g. the translation illustrated in FIGS. 4A-4E, which is represented by a translated distance 418 in FIG. 4E. In some embodiments, the linear actuator, which is coupled to the syringe carrier, translates the syringe conveyor by translating the syringe carrier. It is noted that the rotation of the syringe conveyor is mechanically derive from the translation of the syringe conveyor, as will be clarified below, with reference to FIGS. 5A-5F and 6A-6F. Accordingly, both the translation and the rotation may be accomplished by the same linear actuator 414.

Further to understanding what are translation and rotation and how they are utilized in bringing a syringe to its target position and orientation, attention is drawn now to explaining mechanisms enabling translation and rotation according to certain embodiments of the invention.

In some embodiments, the rotation is mechanically derived from the translation as follows: The supporting module and the syringe conveyor comprise a first member and a second member, respectively. In some embodiments, the second member is comprised in the syringe carrier. The first member and the second member are configured to engage each other during the translation of the syringe conveyor relative to the supporting module, and to cause the syringe conveyor to rotate relative to the supporting module while the first and second members are engaged. In some embodiments, the first and second members may be a rack and a pinion, respectively, as known in the art. In some embodiment, the first member may be a protrusion or a plurality of protrusions, and the second member may be a socket or a plurality of sockets, wherein the socket or the plurality of sockets is configured to engage the protrusion or the plurality of protrusions. A protrusion may be a pin, or a wheel, or any other article suitable for being engaged by a socket, and a socket may be an opening, a cavity, a trail, or any other structure suitable for engaging a protrusion.

Figure 5A:
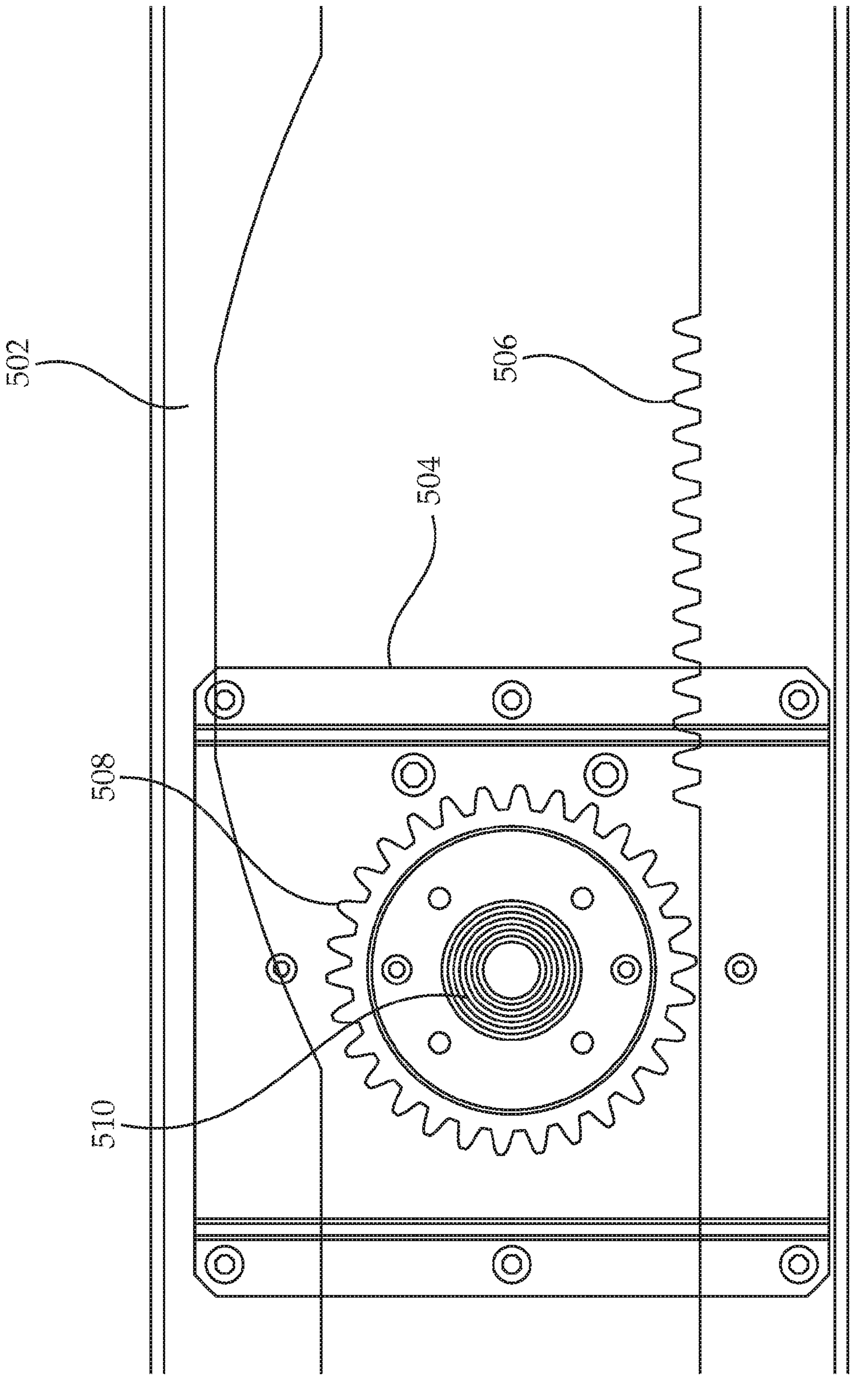
FIGS. 5A-5F schematically illustrate a supporting module and a syringe carrier comprising a rack and a pinion, according to some embodiments of the invention.
Figure 5B:
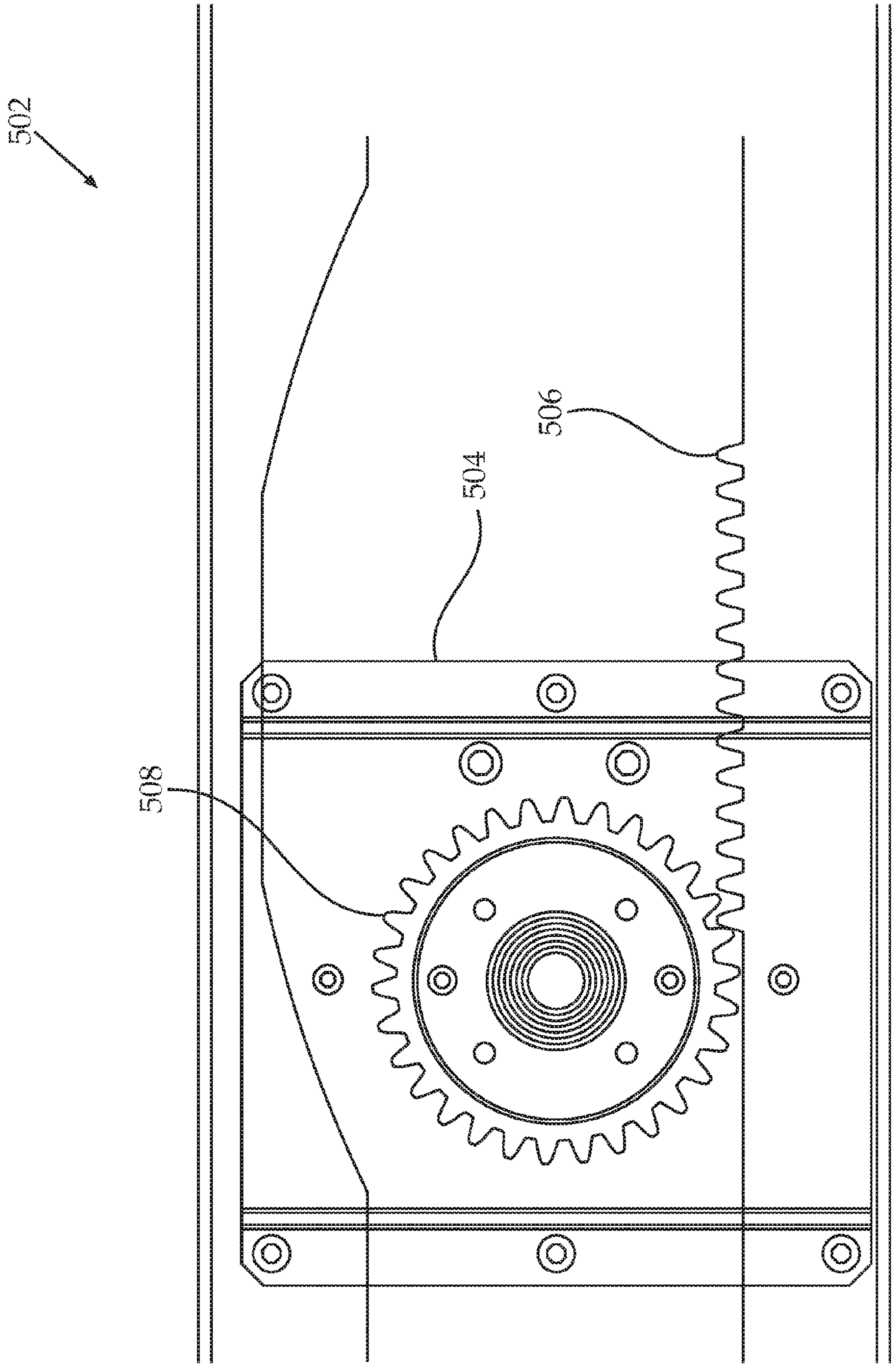
Figure 5C:
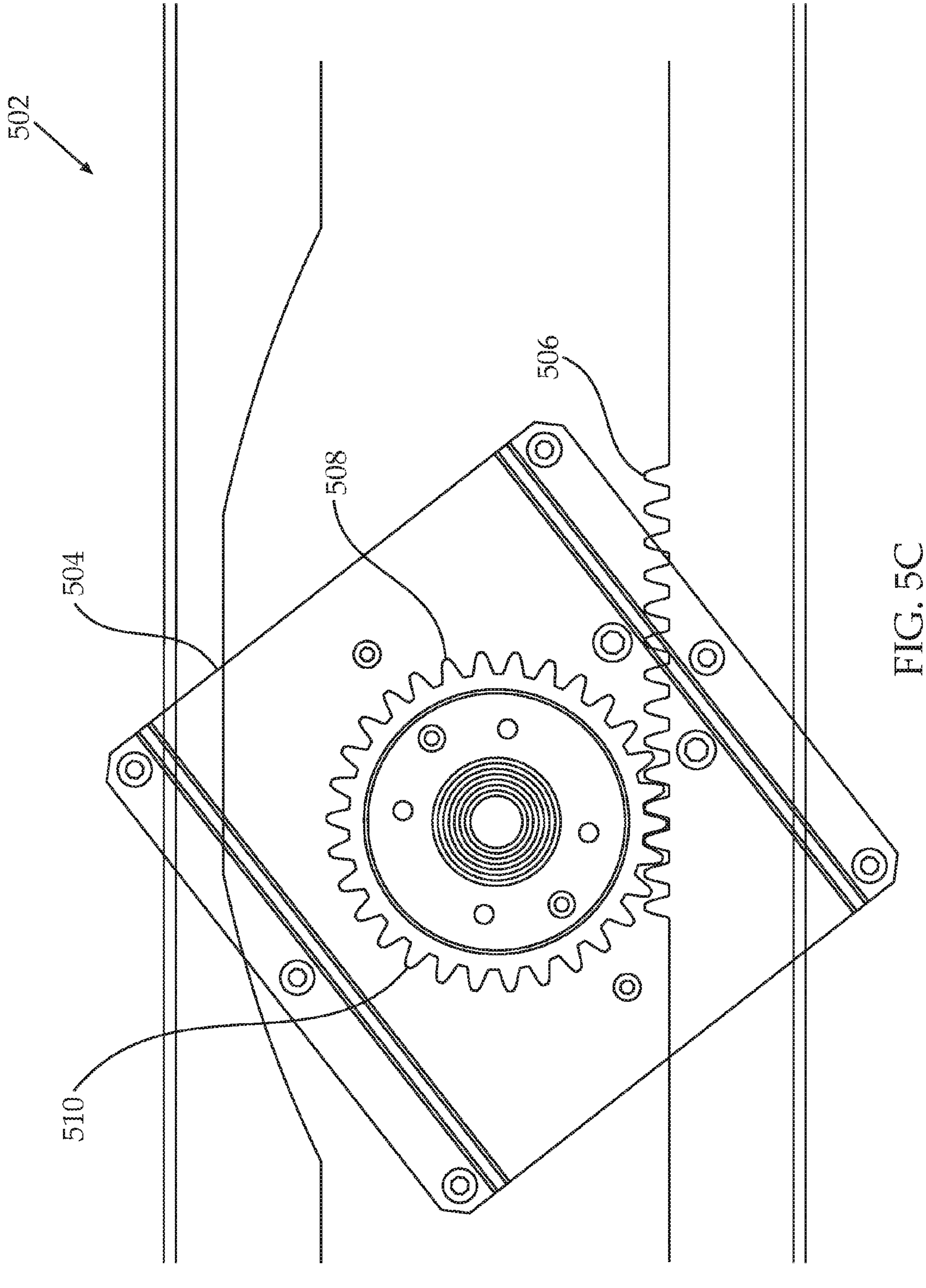
Figure 5D:
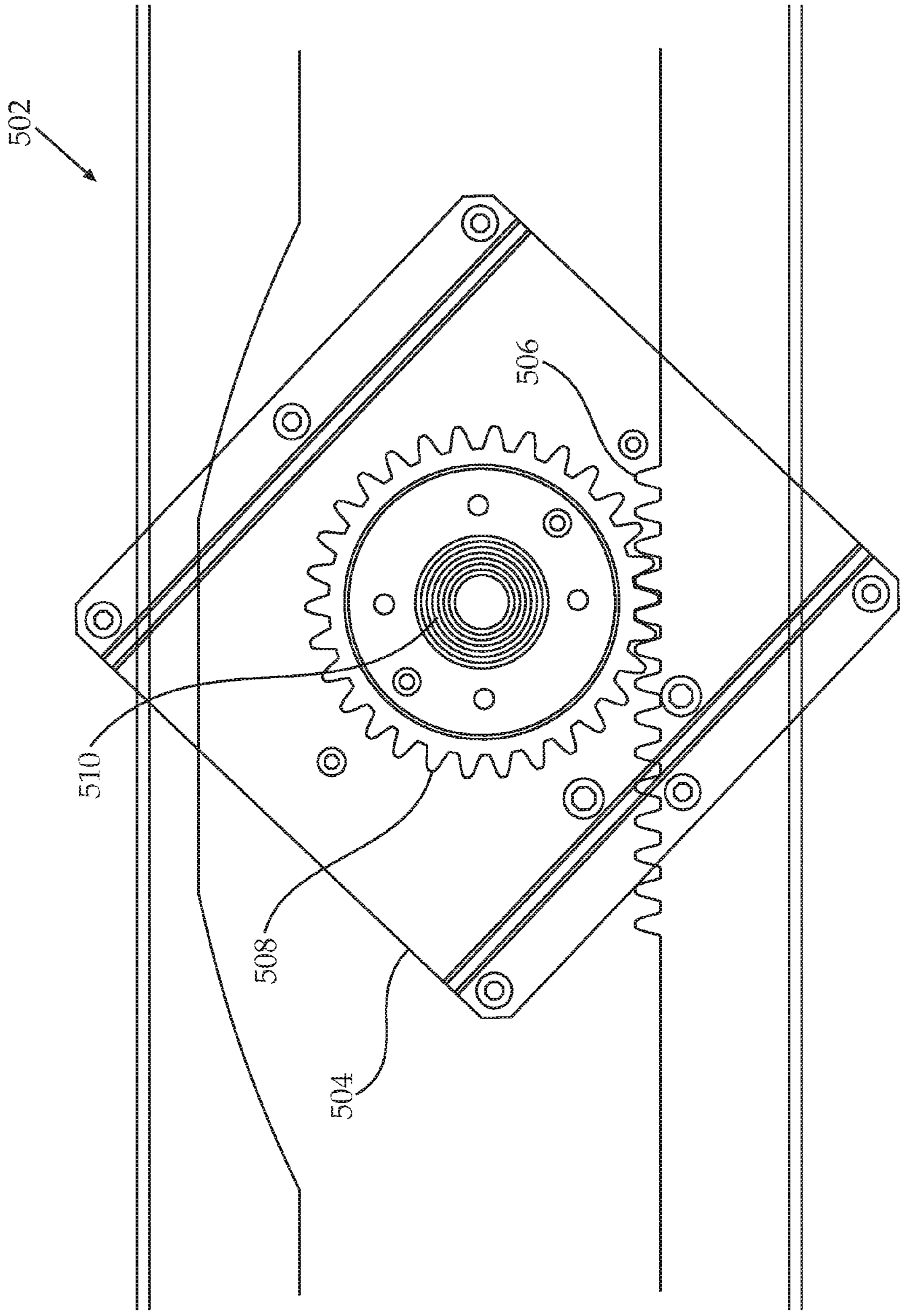
Figure 5E:
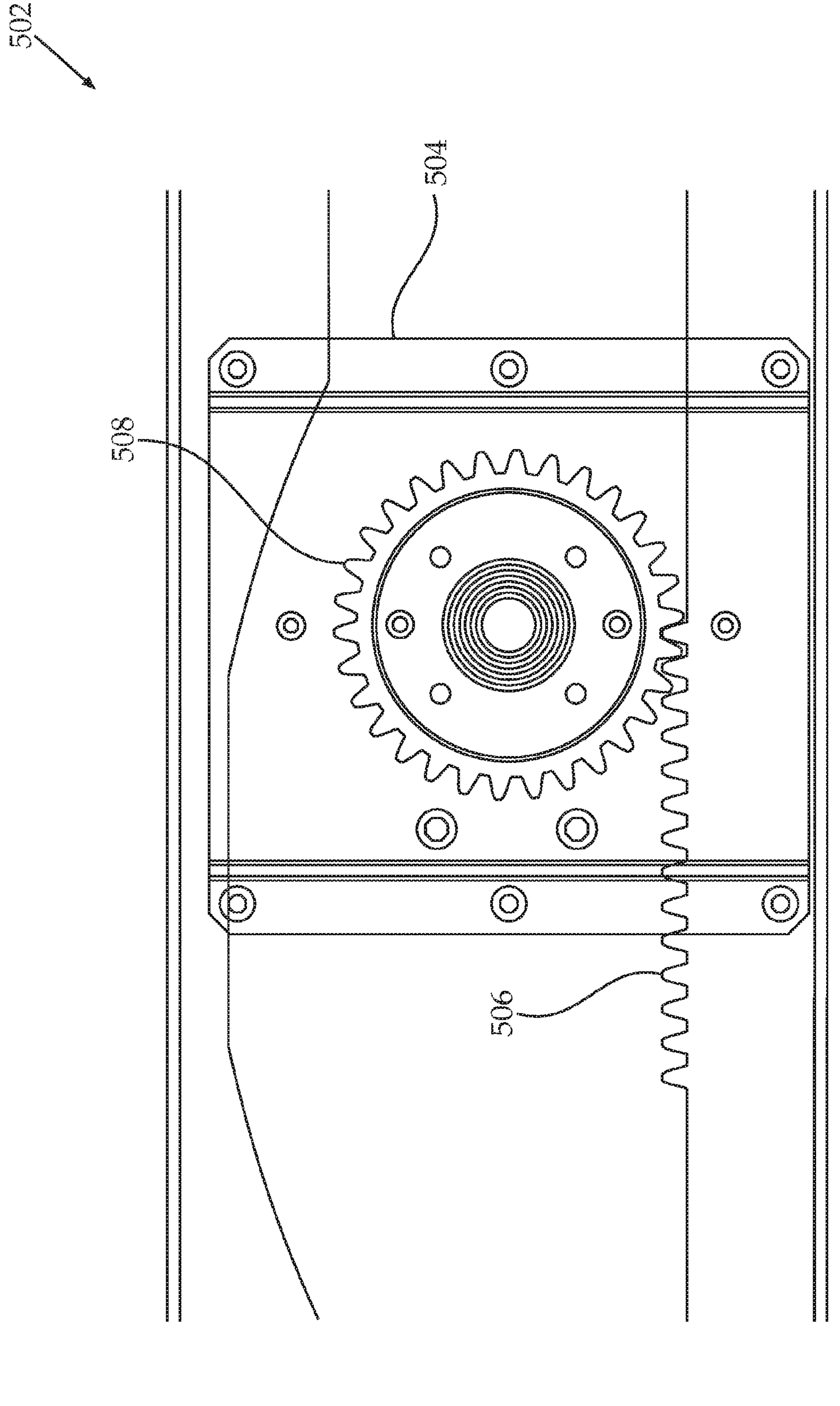
Figure 5F:
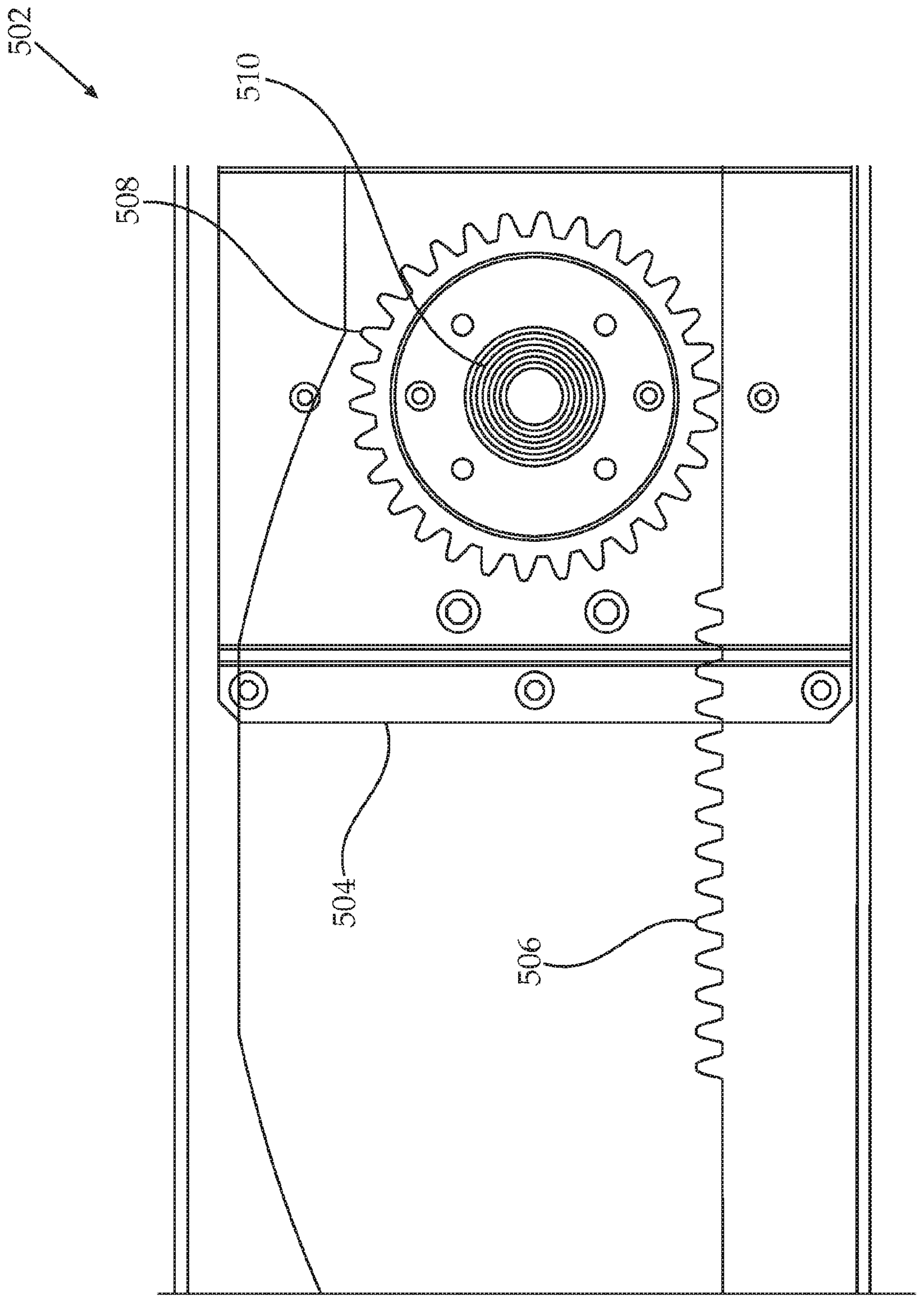

FIGS. 5A to 5E schematically illustrate a supporting module 502 and a syringe carrier 504 comprising a rack 506 and a pinion 508, respectively, according to certain embodiments of the invention. The supporting module 502 and the carrier 504 may be examples of the supporting module 408 and the syringe carrier 410 in FIGS. 4A to 4E. The supporting module 502 supports the syringe carrier 504 by pivot 510, located at the center of the pinion. During the translation of the syringe carrier relative to the supporting module, the teeth of the pinion 508 engage the teeth of the race 506, thereby causing the syringe carrier to rotate around the pivot 510. FIG. 5A schematically illustrates the initial position of syringe carrier 504; FIG. 5B depicts the syringe carrier further to a translation thereof, wherein the pinion starts to engage the pinion; FIGS. 5C and 5D depict two snapshots along the rotation of the syringe carrier, which is caused by the interaction between rack and the pinion; and FIG. 5E schematically illustrates the target position of the syringe carrier.

Figure 6A:
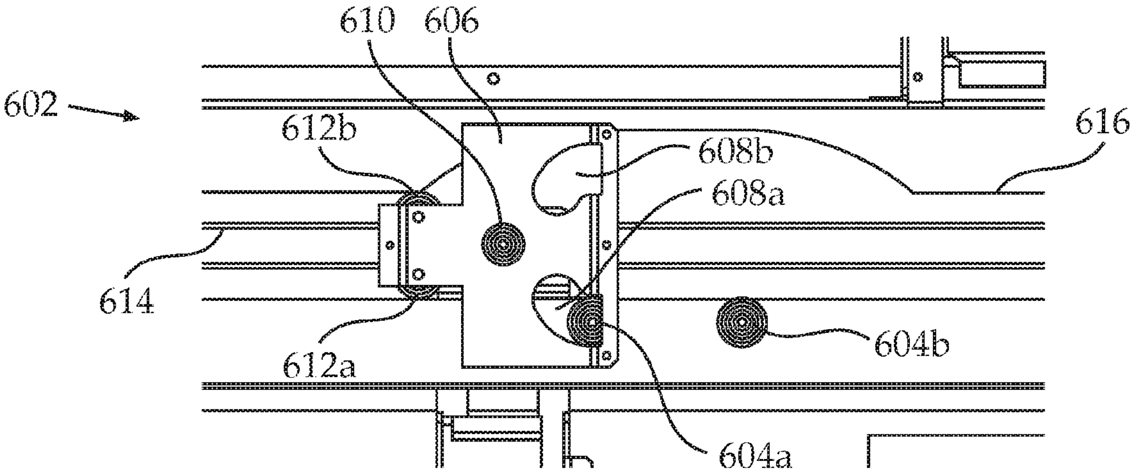
FIGS. 6A-6F schematically illustrate a supporting module comprising protrusions and a syringe carrier comprising sockets, according to some embodiments of the invention.
Figure 6B:
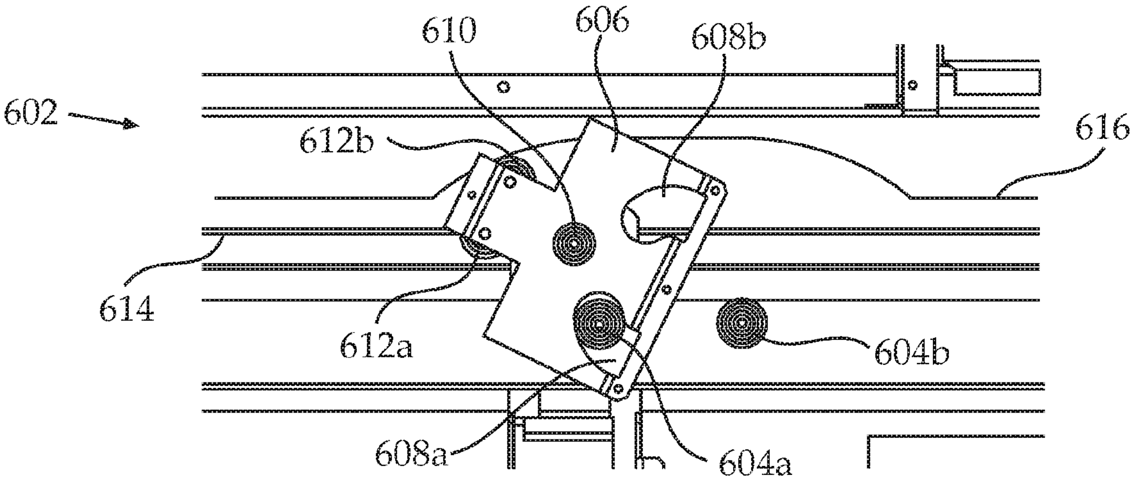
Figure 6C:
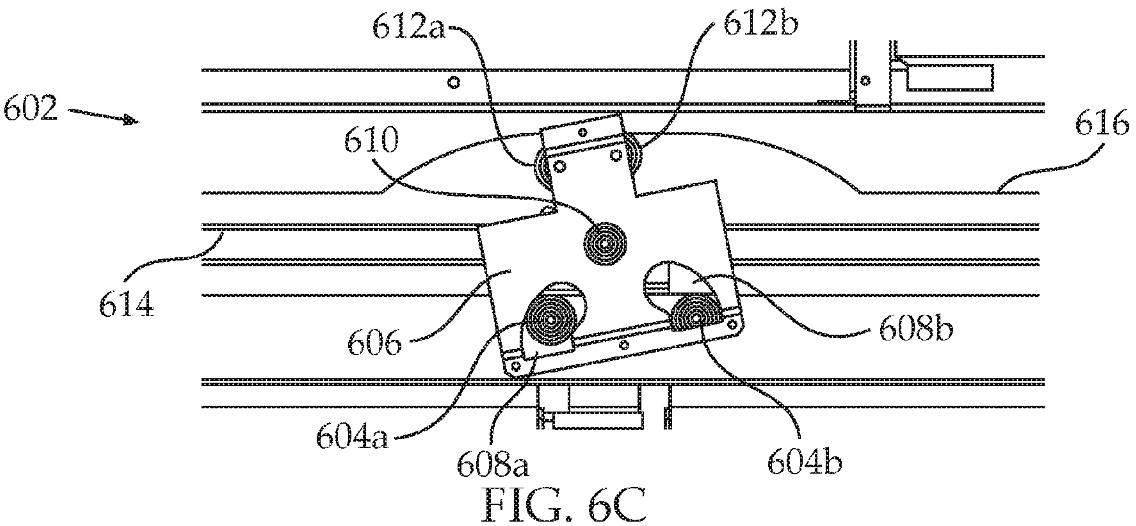
Figure 6D:
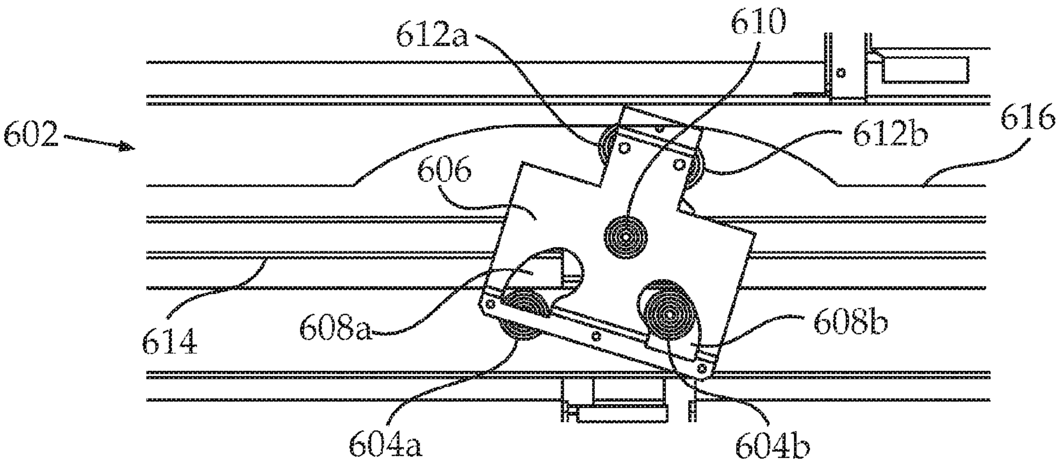
Figure 6E:
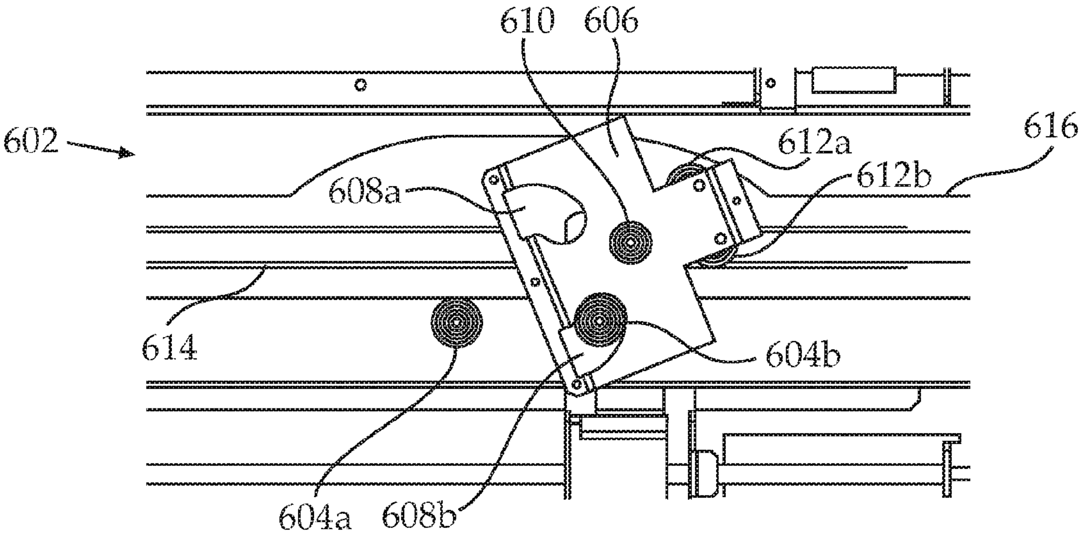
Figure 6F:
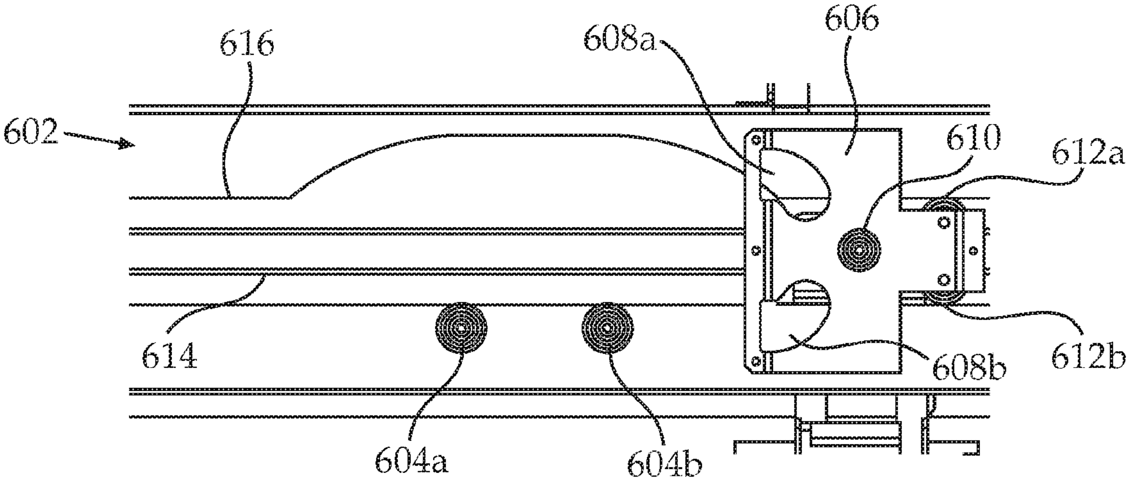
Figure 7A:
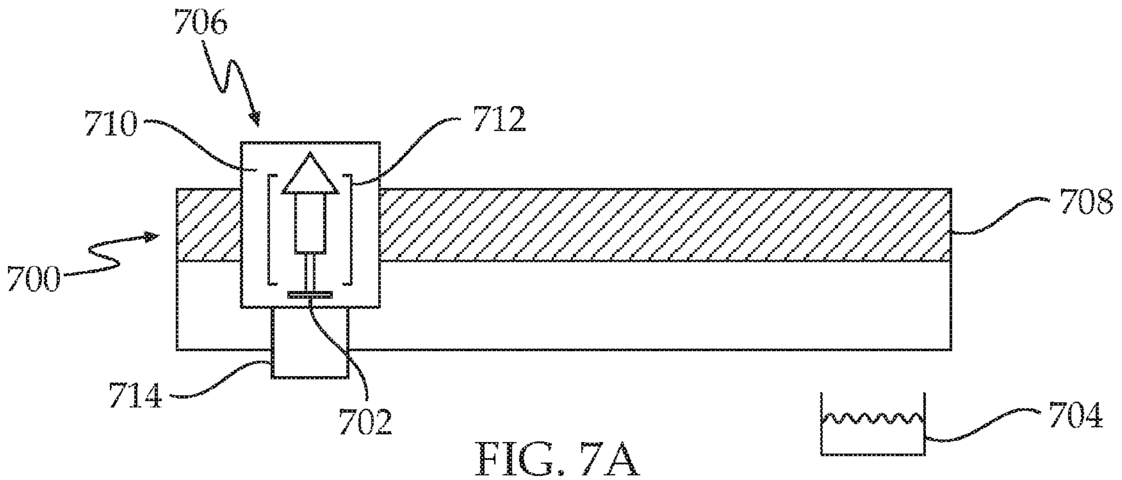
FIGS. 7A-7E schematically illustrate a device for automatically positioning a syringe relative to a container in an upward orientation suitable for drawing medication from the container, according to some embodiments of the invention.
Figure 7B:
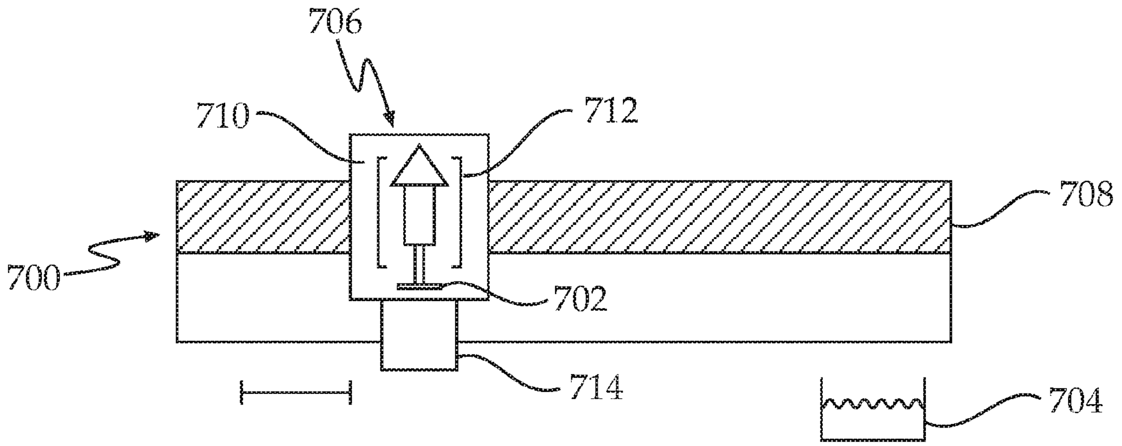
Figure 7C:
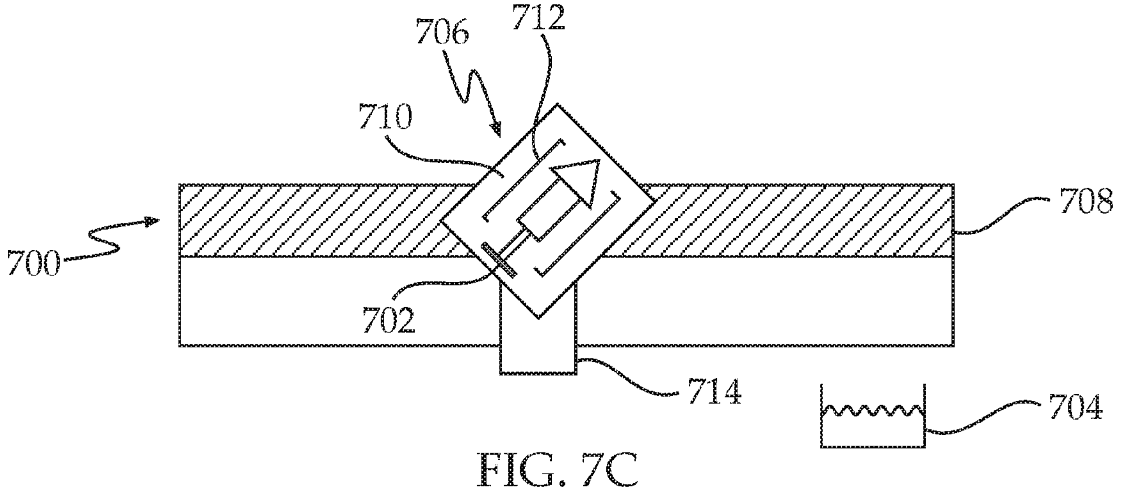
Figure 7D:
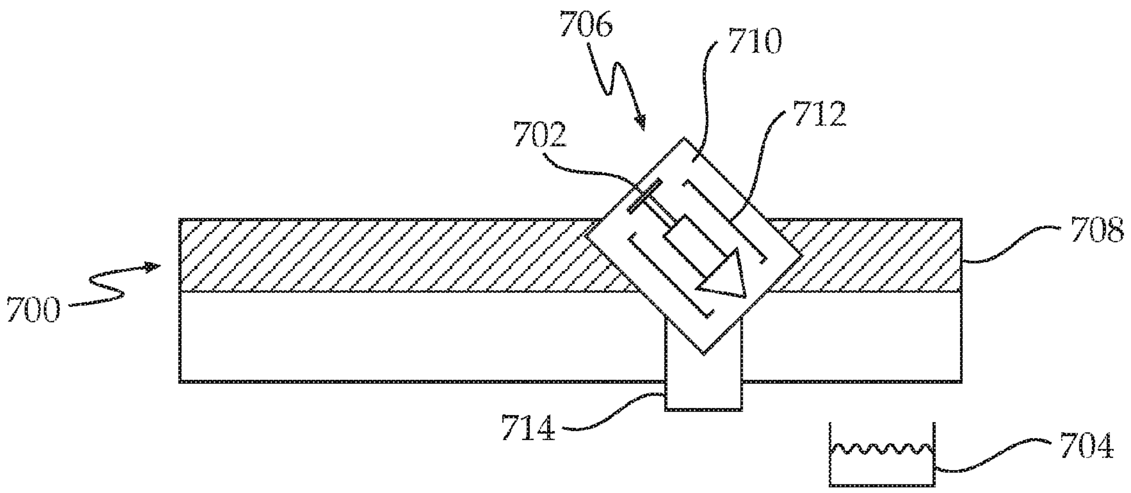
Figure 7E:
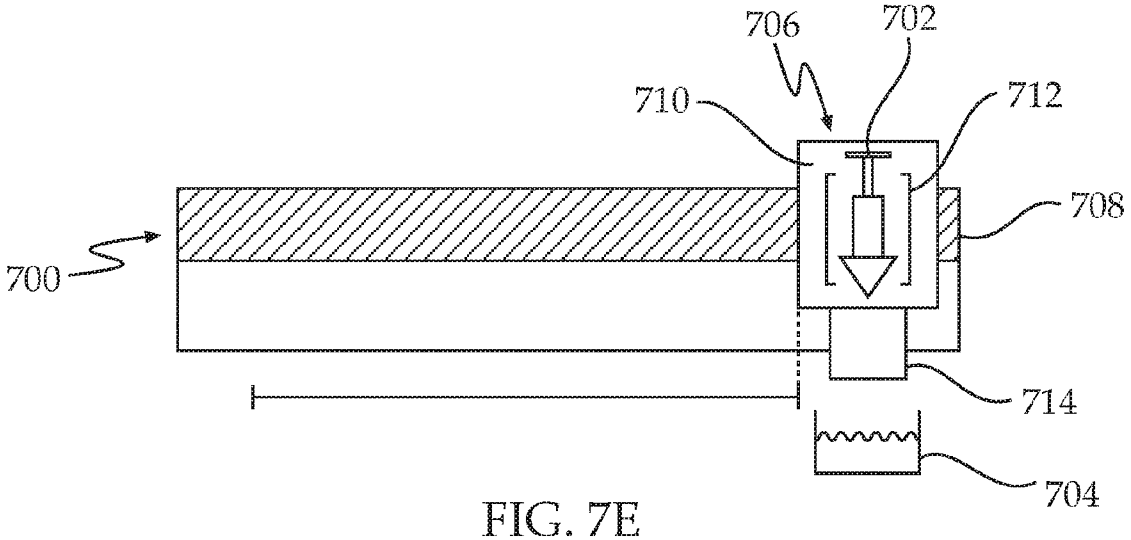

FIGS. 6A to 6F schematically illustrate a supporting module 602 comprising protrusions 604*a* and 604*b* and a syringe carrier 606 comprising sockets 608*a* and 608*b*, according to certain embodiments of the invention. The supporting module 602 and the syringe carrier 606 may be examples of the supporting module 408 and the syringe carrier 410 in FIGS. 4A to 4E. The syringe carrier further comprises a central pivot 610 and two guiding pivots 612*a* and 612*b*. The supporting module further comprises a rail 614, which supports the central pivot, and a guiding trail 616, which limits the movement of the guiding pivots. The rail and the central pivot jointly enable horizontal translation and rotation of the syringe carrier relative to the supporting module. During the translation of the syringe carrier relative to the supporting module, sockets 608*a* and 608*b* engage the protrusions 506*a* and 506*b*, respectively, thereby causing the syringe carrier to rotate around pivot 510. The guiding trail and the guiding pivots jointly limit the rotation of the syringe carrier, thereby preventing undesired rotation (e.g., when the protrusions are not engaged by the sockets. FIG. 6A schematically illustrates the position of the syringe carrier further to a translation thereof, wherein protrusions 604*a* starts to engage socket 608*a*. FIGS. 6B to 6E depict snapshots along the rotation of the syringe carrier, which is caused by the interaction between the protrusions and the sockets; and FIG. 6F schematically illustrates the target position of the syringe carrier.

Further to understanding the structure and way of operation of devices for automatically positioning a syringe relative to a container in a downward orientation, it is appreciated that devices for automatically positioning a syringe relative to a container in an upward orientation may be implemented, utilizing similar structure and way of operation.

FIGS. 7A-7E schematically illustrate a device 700 for automatically positioning a syringe 702 relative to a container 704 in an upward orientation suitable for drawing medication from the container, according to certain embodiments of the invention. The syringe 702 may be an example of syringe 100 in FIG. 1, or any other syringe suitable for the case. Container 704 may be an example of container 304 in FIG. 3. It may be an open ampoule, or any other container suitable for the case, requiring an upward syringe to withdraw a medication therefrom. Device 700 may resemble device 400 in FIG. 4, with appropriate modification due to the difference of the target orientation.

Device 700 comprises a syringe conveyor 706, which is configured to receive the syringe in an initial orientation, which is different from the upward orientation, and to hold the syringe in a steady orientation relative to the syringe conveyor, i.e., wherein the orientation of syringe changes together with the orientation of the syringe conveyor. The syringe conveyor is further configured to be translated and to be rotated while holding the syringe, thereby bringing the syringe to a target orientation, which is an upward orientation above the container. The translation and rotation of the syringe conveyor, while holding the syringe, are schematically illustrated in FIGS. 7A-7E.

Device 700 further comprises a supporting module 708, which is configured to support the syringe conveyor 706, while allowing the syringe conveyor to be translated and rotated. Furthermore, the supporting module is jointly configured with the syringe conveyor so that the rotation of the syringe conveyor is mechanically derived from the translation of the syringe conveyor.

In some embodiments, syringe conveyor 706 may comprise a syringe carrier 710 and a syringe holder 712. In some embodiments, device 700 may comprise a linear actuator 714 coupled to the supporting module and to the syringe conveyor, and configured to translate the syringe conveyor relative to the supporting module. In some embodiments, the linear actuator, which is coupled to the syringe carrier, translates the syringe conveyor by translating the syringe carrier.

In some embodiments, the syringe conveyor comprise a first member and a second member, respectively, jointly configured to engage each other during the translation of the syringe conveyor relative to the supporting module, and to cause the syringe conveyor to rotate relative to the supporting module while the first and second members are engaged. In some embodiments, the first and second members may be a rack and a pinion, respectively, for example the rack and pinion illustrated in FIGS. 5A to 5E described above. In some embodiment, the first member may be a protrusion or a plurality of protrusions, and the second member may be a socket or a plurality of sockets, for example the protrusions and sockets illustrated in FIGS. 6A to 6F described above.

Returning to FIGS. 2A to 2D and 3A to 3D, it is noted that further to positioning the syringe in a suitable orientation relative to the container, filling the syringe comprises reducing the distance between the syringe and the container, until the needle reaches the medication residing therein, and pulling the plunger out of the barrel 214, thereby withdrawing medication from the container into the barrel. In the following paragraphs, devices for pulling the plunger are depicted.

FIGS. 8A to 8D schematically illustrate a device 800 for holding a barrel 802 of a syringe 804 and a plunger 806 of the syringe, in order to allow automatic displacement of the plunger inside the barrel, according to certain embodiments of the invention. Syringe 804 may be an example of syringe 100 in FIG. 1, or any other syringe suitable for the case.

Device 800 comprises a syringe holder 808 configured to hold the syringe, gripper 810 configured to engage the plunger, thereby enabling automatic displacement (pulling) of the plunger out of the barrel. In some embodiments, the gripper is configured to engage and pull a top 812 of the syringe. Device 800 further comprises a lock mechanism configured to maintain the barrel of the syringe in a steady position relative to the syringe holder, thereby enabling the automatic pulling of the plunger relative to the barrel. In some embodiments, the lock mechanism may be comprised by or coupled to the syringe holder. In other embodiments, the lock mechanism may be comprised in a gripper holder, as explained further below. Additionally or alternatively, any other lock mechanism suitable for the case may be utilized.

Figure 8A:
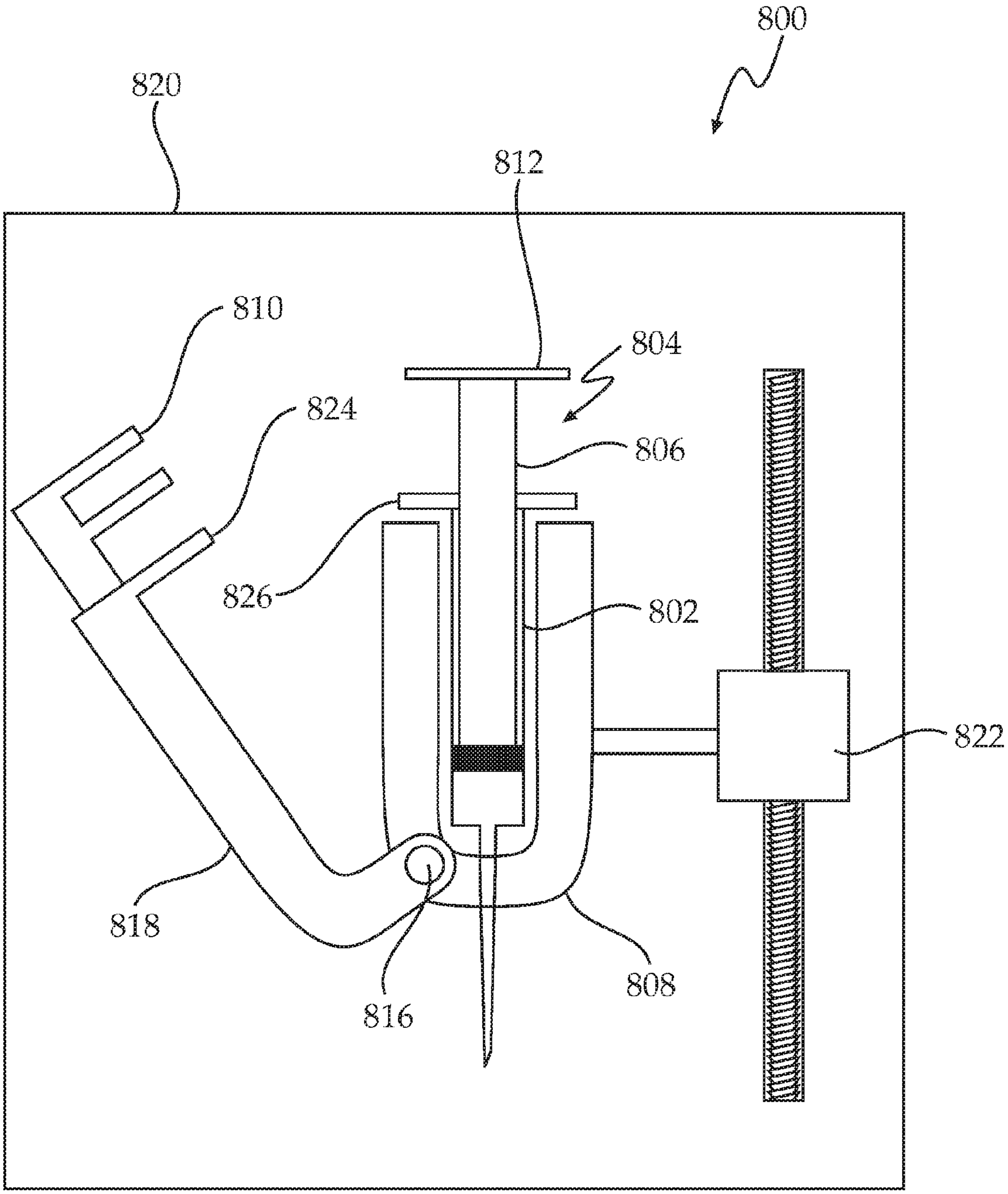
FIGS. 8A-8D schematically illustrate a device for holding a barrel of a syringe and a plunger of the syringe, in order to allow automatic displacement of the plunger inside the barrel, according to some embodiments of the invention.
Figure 8B:
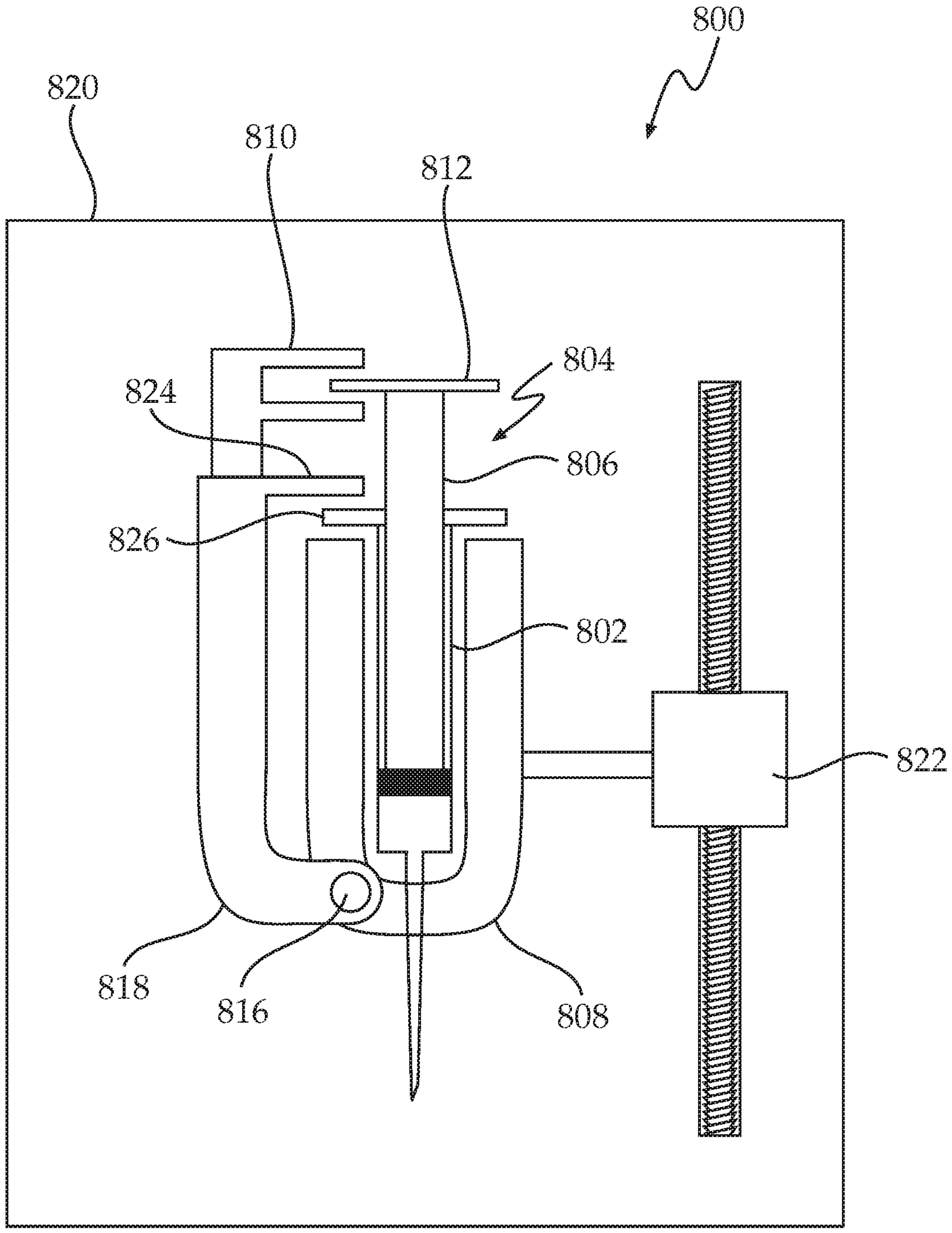

The gripper is configured to engage the plunger as follows: the gripper and the syringe holder are coupled to each other, and are jointly configured to change their relative angle with respect to each other, thereby enabling the gripper to engage the plunger. In FIGS. 8A and 8B, for example, the "lower" ends of the syringe holder and the gripper are coupled by a pivot 816, while their "upper" ends are able to move with respect to each other. In FIG. 8A, the "upper" ends are relatively distant from each other, thereby allowing placing a syringe into the holder or removing it therefrom. In FIG. 8B, the "upper" ends of the gripper and the syringe holder are close to each other, thereby enabling the gripper to engage the top 812 of the syringe.

In some embodiments, device 800 further comprises a gripper holder 818 configured to hold the gripper. The gripper holder and the syringe holder are coupled to each other, and are jointly configured to change their relative angle with respect to each other, thereby enabling the gripper to engage the plunger. In some embodiments, the gripper holder and the syringe holder are jointly configured to be translated in parallel to each other, and to be rotated relative to each other, thereby changing the relative angle.

In some embodiments, the lock mechanism comprises a locking flange 824 coupled to the gripper holder. When the "upper" ends of the gripper and the syringe holder are close to each other, as illustrated in FIG. 8B, the locking flange 824 engage the syringe flange 826 of the syringe, thereby keeping the barrel of the syringe within the syringe holder.

In some embodiments, device 800 may further comprise a syringe carrier 820 configured to support the syringe holder and the gripper holder. The syringe carrier 820 may be an example of the syringe carrier 410 in FIGS. 4A-4E, the syringe carrier 504 in FIGS. 5A-5F, the syringe carrier 606 in FIGS. 6A-6F, the syringe carrier 710 in FIGS. 7A-7E, or any other syringe carrier suitable for the case. The syringe carrier 820 is further configured to allow a translation of the syringe holder and the gripper holder with respect to the syringe carrier, and to allow a relative rotation of the syringe holder and the gripper holder with respect to each other. In some embodiments, the syringe carrier, the syringe holder, and the gripper holder, are jointly configured to mechanically derive the relative rotation of gripper holder and the syringe holder with respect to each other from the parallel translation of the gripper holder and the syringe holder relative to the syringe carrier.

In some embodiments, device 800 further comprises a linear actuator 822 coupled to the syringe carrier, the syringe holder, and the gripper holder. The linear actuator is configured to drive the parallel translation of the parallel translation of the gripper holder and the syringe holder relative to the syringe carrier. It is noted that since the relative rotation is mechanically derive from the parallel translation, both the parallel translation and the relative rotation may be accomplished by the same linear actuator 822.

Recalling the mechanisms described with reference to FIGS. 4A to 4E, for deriving rotation from translation, it is appreciated that similar mechanisms may be utilized in embodiments of device 800. In some embodiments, the syringe carrier may comprise a first member, the gripper holder may comprise a second member, wherein the first and second members are jointly configured to be engaged during the parallel translation, thereby causing a rotation of the gripper holder. Additionally or alternatively, the he syringe carrier may comprise a third member, the syringe holder may comprise a fourth member, wherein the third and third members are jointly configured to be engaged during the parallel translation, thereby causing a rotation of the syringe holder. In some embodiment, the first member and/or the third member may be a rack, and the second member and/or the fourth member may be a pinion. In some embodiment, the first member and/or the third member may be a protrusion, and the second member and/or the fourth member may be a socket, for example a trail. In some embodiment, the second member and/or the fourth member may be a protrusion, and the first member and/or the third member may be a socket, for example a to trail.

Figure 8C:
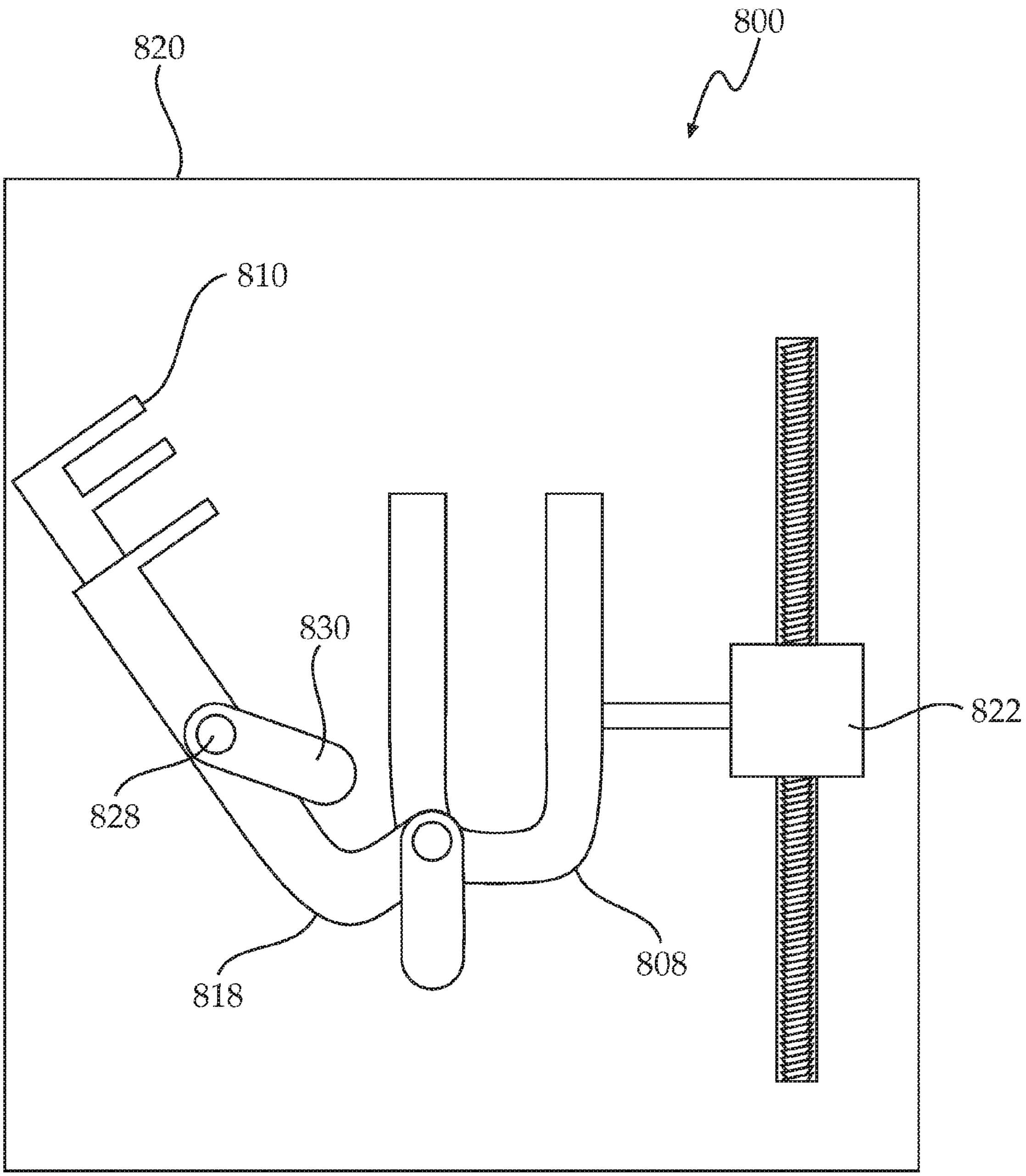
Figure 8D:
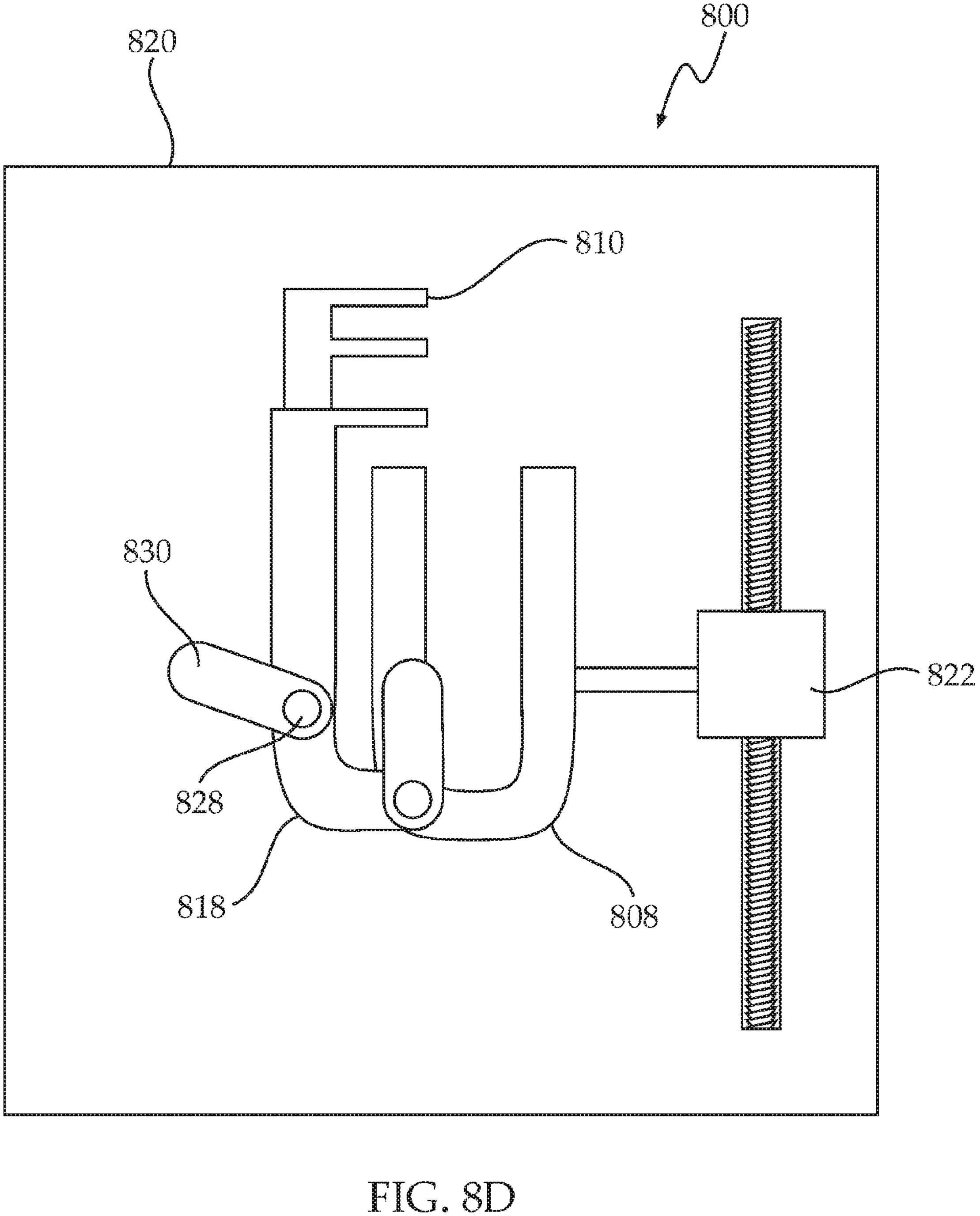

FIGS. 8C and 8D schematically illustrate an example of a protrusion 828, and a trail 830 configured to guide the movement of the protrusion relative to the trail. In this example, the trail is comprised in the syringe carrier, and the protrusion is comprised in the gripper holder. The gripper holder is translated relatively to syringe carrier, by translation of pivot 816. During the translation, the trail guides the gripper holder to rotate around the pivot, thereby changing its angle relative to the syringe holder. It should be appreciated, though, that FIGS. 8C and 8D are brought as a non-limiting example, and other embodiments, for examples embodiments wherein the syringe holder is being rotated, or any other embodiment suitable for the case, may be implemented.

Further to reading the above description of some embodiments of devices for carrying out operation related to automatic filling of syringes with medications, attention it now drawn to embodiments of systems utilizing devices jointly configured for automatic filling of syringes.

Figure 9:
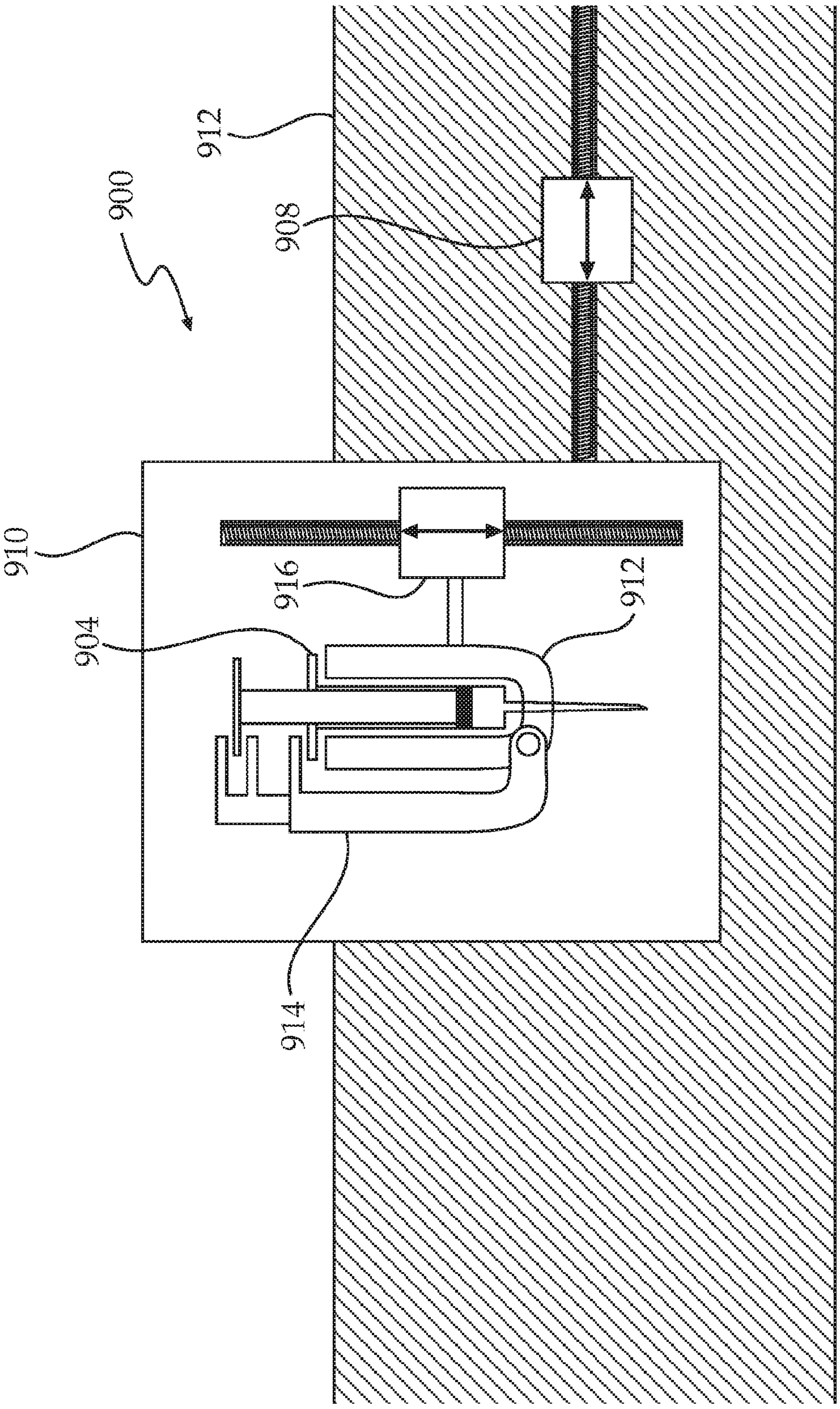
FIG. 9 schematically illustrates a system for automatically drawing medication from a container into a syringe, according to some embodiments of the invention.

FIG. 9 schematically illustrates a system 900 for automatically drawing medication from a container into a syringe 904, according to some embodiments of the invention. The syringe 904 may be, for example, syringe 100 in FIG. 1, or any other syringe suitable for the case. The container may be, for example, container 204 in FIG. 2, container 304 in FIG. 3, or any other container suitable for the case.

System 900 comprises a first device configured to receive the syringe in an initial orientation, and to automatically position the syringe in a target orientation suitable for drawing medication from the container. In some cases, the target orientation is the upward orientation, as described, e.g., in reference to FIG. 2. In some cases, the target orientation is the downward orientation, as described, e.g., in reference to FIG. 3. The syringe is automatically positioned in the target orientation by utilizing a first translation and by further utilizing a first rotation, wherein the first rotation is mechanically derived from the first translation. Therefore, both the first translation and the first rotation may be obtained by utilizing the first actuator 908. The first device may be, for example, the device 400 of FIGS. 4A-4E, the device 700 of FIGS. 7A-7E, or any other device suitable for the case. Moreover, further to understanding the structure and operation of the devices 400 and 700, it should be appreciated that features and variants of devices 400 and 700 may be applicable as well to the first device of system 900. For example, the first device may comprise a syringe conveyor 910 and a support 912, with structure and operation similar to the syringe conveyors and supporting modules described with reference to FIGS. 4A-4E, the device 700 of FIGS. 7A-7E.

System 900 further comprises a second device 910 configured to allow an automatic displacement of a plunger of the syringe inside a barrel of the syringe by holding the barrel, holding the plunger, and translating the plunger relative to the barrel. The second device may be, for example, the device 800 of FIGS. 8A-8D, or any other device suitable for the case. Moreover, further to understanding the structure and operation of the devices 800, it should be appreciated that features and variants of devices 800 may be applicable as well to the second device of system 900. For example, in some embodiments, the second device may comprise a syringe holder 912 and a gripper 914, similar to the syringe holder and the gripper of device 800. In some embodiments, the gripper is configured to engage the plunger by utilizing a relative rotation of the gripper and a syringe holder relative to each other. In some embodiment, the relative rotation is mechanically derived from a parallel translation thereof. Therefore, in some embodiments, the second device enables automatic engaging of the plunger by the gripper while utilizing a second linear actuator 916.

The system 900 further comprises a third device configured to enable a needle coupled to the syringe, whereupon the syringe is held in the target orientation, to reach the medication in the container by reducing a distance between the container and the syringe. The distance may be reduced by advancing the syringe toward the container, and/or by advancing the container toward the syringe. In some embodiments, the third device may be jointly implemented by the syringe holder 912 and the second linear actuator 916, which is configured to translate the syringe holder.

Further to understanding the structure and operation of system 900, it is appreciated that, in some embodiments, the system may be implemented with relatively small horizontal dimensions. In some embodiments, the horizontal dimensions of the system allow placing the system within a rectangular cuboid whose maximal width is 15 centimeters, a rectangular cuboid whose maximal length is 50 centimeters, and/or a rectangular cuboid whose maximal floor area is 1000 square centimeters. In some embodiments, the horizontal dimensions allow placing the system within a rectangular cuboid whose maximal width is 10 centimeters.

The invention claimed is:

1. A device for automatically positioning a syringe in an orientation suitable for withdrawing medication from a container, the device comprising:

a syringe conveyor configured to receive the syringe in an initial orientation, and to bring the syringe to a target orientation by being translated and rotated while holding the syringe in a steady orientation relative to the syringe conveyor, wherein the target orientation, which is suitable for withdrawing medication from the container, is one of an upward orientation and a downward orientation, and the initial orientation is different from the target orientation, and wherein in the upward orientation a tip of the syringe is pointing downward and in the downward orientations the tip is pointing upward; and a supporting module configured to support the syringe conveyor while allowing a translation and a rotation thereof;

wherein the supporting module and the syringe conveyor are jointly configured to mechanically derive the rotation from the translation.

2. The device of claim 1, wherein the syringe conveyor comprises:

a syringe carrier configured to be translated and rotated; wherein the syringe carrier and the supporting module are jointly configured to mechanically derive the rotation from the translation; and a syringe holder configured to hold the syringe in a steady orientation relative to the syringe carrier.

3. The device of claim 1, further comprising:

a linear actuator coupled to the supporting module and to the syringe conveyor, configured to translate the syringe conveyor relative to the supporting module.

4. The device of claim 1, wherein the supporting module comprises a first member, and the syringe conveyor comprises a second member, the first and second members are jointly configured to engage each other during the translation, thereby inducing the rotation.

5. The device of claim 4, wherein the first member is a rack and the second member is a pinion.

6. The device of claim 4, wherein one of the first and second members is a protrusion and another one of the first and second members is a socket configured to engage the protrusion.

7. The device of claim 4, wherein one of the first and second members is a plurality of protrusions, and another one of the first and second members is a plurality of sockets configured to engage the protrusions.

8. A system for automatically drawing medication into a syringe, the system comprising:

a first device configured to receive the syringe in an initial orientation, and to automatically position the syringe in a target orientation suitable for drawing medication from the container by utilizing a first translation and by further utilizing a first rotation mechanically derived from the first translation, wherein the target orientation is one of an upward orientation and a downward orientation, and the initial orientation is different from the target orientation; in the upward orientation a tip of the syringe is pointing downward and in the downward orientations the tip of the syringe is pointing upward;

a second device configured to allow an automatic displacement of a plunger of the syringe inside a barrel of the syringe by holding the barrel, holding the plunger, and translating the plunger relative to the barrel; and a third device configured to enable a needle coupled to the syringe, whereupon the syringe is held in the target orientation, to reach the medication in the container by reducing a distance between the container and the syringe.

9. The system of claim 8, wherein the first device comprises:

a syringe conveyor configured to receive the syringe in the initial orientation, and to bring the syringe to the target orientation by being translated and rotated while holding the syringe in a steady orientation relative to the syringe conveyor; and a supporting module configured to support the syringe conveyor while allowing a translation and a rotation thereof; wherein the first supporting module and the syringe conveyor are jointly configured to mechanically derive the rotation from the translation.

10. The system of claim 9, wherein the syringe conveyor comprises:

a syringe carrier configured to be translated and rotated; wherein the syringe carrier and the supporting module are jointly configured to mechanically derive the rotation from the translation; and a syringe holder configured to hold the syringe in a steady position relative to the syringe carrier.

11. The system of claim 10, wherein the second device comprises:

a lock mechanism configured to stabilize the barrel of the syringe relative to the syringe holder; and a gripper coupled to the syringe holder and jointly configured therewith to enable the gripper to engage the plunger by changing a relative angle between the gripper and the syringe holder;

wherein the gripper, the syringe holder, and the lock mechanism are jointly configured to enable the automatic displacement.

12. The system of claim 11, wherein the second device further comprises a gripper holder configured to hold the gripper; wherein the gripper holder and the syringe holder are jointly configured to be translated in parallel, and to be rotated relative to each other, thereby changing the relative angle; and a syringe carrier configured to support the syringe holder and the gripper holder, to allow a translation of the syringe holder and the gripper holder with respect to the syringe carrier, and to allow a relative rotation of the syringe holder and the gripper holder with respect to each other;

wherein the syringe carrier, the syringe holder, and the gripper holder, are jointly configured to mechanically derive the relative rotation from the translation.

13. The system of claim 8 wherein the first device comprises:

a syringe carrier configured to be translated and rotated; and a syringe holder configured to hold the syringe in a fixed position relative to the syringe carrier.

14. A method for automatically drawing medication into a syringe, the method comprising:

receiving the syringe in an a first orientation;

utilizing a translation and a rotation for automatically positioning the syringe in a second orientation suitable for drawing medication from the container, wherein in one of the first and second orientations a tip of the syringe is pointing downward and in other one of the first and second orientations a tip of the syringe is pointing upward; and wherein the first rotation is mechanically derived from the first translation;

automatically reducing a distance between the container and the syringe, while the syringe is held in the second orientation, thereby enabling a needle coupled to the syringe to reach the medication;

automatically holding a barrel of the syringe; and automatically translating the plunger inside the barrel, thereby drawing medication into a syringe.

* * * * *